United States Patent
Stamler et al.

(10) Patent No.: US 7,229,762 B2
(45) Date of Patent: Jun. 12, 2007

(54) PROTEOMIC SCREENING FOR REDOX STATE DEPENDENT PROTEIN—PROTEIN INTERACTIONS

(75) Inventors: Jonathan S. Stamler, Chapel Hill, NC (US); Akio Matsumoto, Durham, NC (US)

(73) Assignee: Duke University Medical Center, Durham, NC (US)

( * ) Notice: Subject to any disclaimer, the term of this patent is extended or adjusted under 35 U.S.C. 154(b) by 559 days.

(21) Appl. No.: 10/378,419

(22) Filed: Mar. 3, 2003

(65) Prior Publication Data

US 2004/0072257 A1      Apr. 15, 2004

(51) Int. Cl.
- C12Q 1/68 (2006.01)
- G01N 33/53 (2006.01)
- C12N 5/00 (2006.01)
- C12N 5/02 (2006.01)
- C12N 15/63 (2006.01)

(52) U.S. Cl. ............... 435/6; 435/7.31; 435/325; 435/375

(58) Field of Classification Search ............... None
See application file for complete search history.

(56) References Cited

U.S. PATENT DOCUMENTS

| | | | |
|---|---|---|---|
| 6,083,693 | A | 7/2000 | Nandabalan et al. |
| H1892 | H | 10/2000 | Klein et al. |
| 6,159,705 | A | 12/2000 | Trueheart et al. |
| 6,187,535 | B1 | 2/2001 | LeGrain et al. |
| 2002/0098511 | A1 | 7/2002 | Heichman et al. |
| 2002/0160361 | A1 | 10/2002 | Loehrlein et al. |

FOREIGN PATENT DOCUMENTS

WO    WO 00/29848    5/2000

OTHER PUBLICATIONS

Dedio et al. NOSIP, a novel modulator of endothelial nitric oxide synthase activity. FASEB 15: 79-89. 2001.*
Kurimoto et al. Growth inhibition and radiosensitization of cultered glioma cells by nitric oxide generating agents. J. of Neuro-oncology 42:35-44. 1999.*
Mendoza-Alvarez et al. Poly(ADP-ribose) Polymerase is a Catalytic Dimer and the Automodification Reaction is Intermolecular. J. Biol. Chem. 268 (30): 22575-22580. 1993.*
Almeida et al. (2001). Proc. Natl. Acad. Sci. USA 98: 15294-15299.
Bredt et al. (1992). J. Biol. Chem. 267: 10976-10981.
Bulotta et al. (2001). J. Biol. Chem. 276: 6529-6536.
Cocchi et al. (2000). Proc. Natl. Acad. Sci. USA 97: 13812-13817.
De Nadai et al. (2000). Proc. Natl. Acad. Sci. USA 97: 5480-5485.
Dimmeler et al. (1997). J. Exp. Med. 185: 601-607.
Eu et al. (2000). Biochemistry 39: 1040-1047.
Ferlinz et al. (1994). Biochem. J. 301: 855-862.
Gavin et al. (2002). Nature 415: 141-147.
Haneline et al. (1998). Blood 91: 4092-4098.
Hermann et al. (1997). Int. J. Immunopharmacol. 19: 387-397.
Ho et al. (2002). Nature 415: 180-183.
Hunter (2000). Cell 100: 113-127.
Hurwitz et al. (1994). J. Biol. Chem. 269: 5440-5445.
Huwiler et al. (1999). J. Biol. Chem. 274: 7190-7195.
Igarashi et al. (1999). Proc. Natl. Acad. Sci. USA 96: 12583-12588.
Kim et al. (1997). J. Biol. Chem. 49: 31138-31148.
Kumar and Snyder (2002). Nature 415: 123-124.
Lee et al. (1995). Immunogenetics 41: 263-270.
Lipton and Bossy-Wetzel (2002). Cell 111: 147-150.
Liu and Anderson (1995). J. Biol. Chem. 270: 27179-27185.
Liu et al. (2000). Proc. Natl. Acad. Sci. USA 97: 4672-4676.
Mannick et al. (1994). Cell 79: 1137-1146.
Mannick et al. (1999). JAIDS 22: 1-9.
Mannick et al. (1999). Science 284: 651-654.
Mannick et al. (2001). J. Cell Biol. 154: 1111-1116.
Marshall and Stamler (2002). J. Biol. Chem. 277: 34223-34228.
Nathan and Xie (1994). Cell 78: 915-918.
Romiti et al. (2000). Mol. and Cell. Biochem. 205: 75-81.
Schmidt and Richter (2000). Dev. Genes Evol. 210: 575-578.
Schwandner et al. (1998). J. Biol. Chem. 273: 5916-5922.
Sessa et al. (1995). J. Biol. Chem. 270: 17641-17644.
Stamler et al. (1997). Neuron 18: 691-696.
Stamler et al. (2001). Cell 106: 675-683.
Takeda et al. (1999). J. Biol. Chem. 274: 10654-10660.
Zech et al. (1999). J. Biol. Chem. 274: 20931-20936.
Zhu et al. (2001). Science 293: 2101-2105.
Zhang et al. (1997). Science 276: 1268-1272.
Kunsch and Medford (1999). Circulation Res. 85: 753-766.
Rain et al. (2001). Nature 409: 211-215.
International Search Report for PCT/US02/31571 corresponding to U.S.S.N.: 10/378,419, mailed Apr. 29, 2003.
Delneri et al. (2001). Curr. Opin. Biotechnol. 12: 87-91.
Fung et al. (2001). Curr. Opin. Biotechnol. 12: 65-69.

* cited by examiner

Primary Examiner—Nancy Vogel
Assistant Examiner—Michele K. Joike
(74) Attorney, Agent, or Firm—Mintz, Levin, Cohn, Ferris, Glovsky and Popeo, P.C.

(57) ABSTRACT

This invention provides a modified yeast two-hybrid system in order to identify NO-dependent protein-protein interactions. Bait proteins implicated in apoptotic signaling pathways were used to identify NO-dependent interactions. The physiological relevance of these interactions is demonstrated by their occurrence and dependence on endogenous NO in mammalian cells, and by the functional interrelatedness of bait and prey.

53 Claims, 5 Drawing Sheets

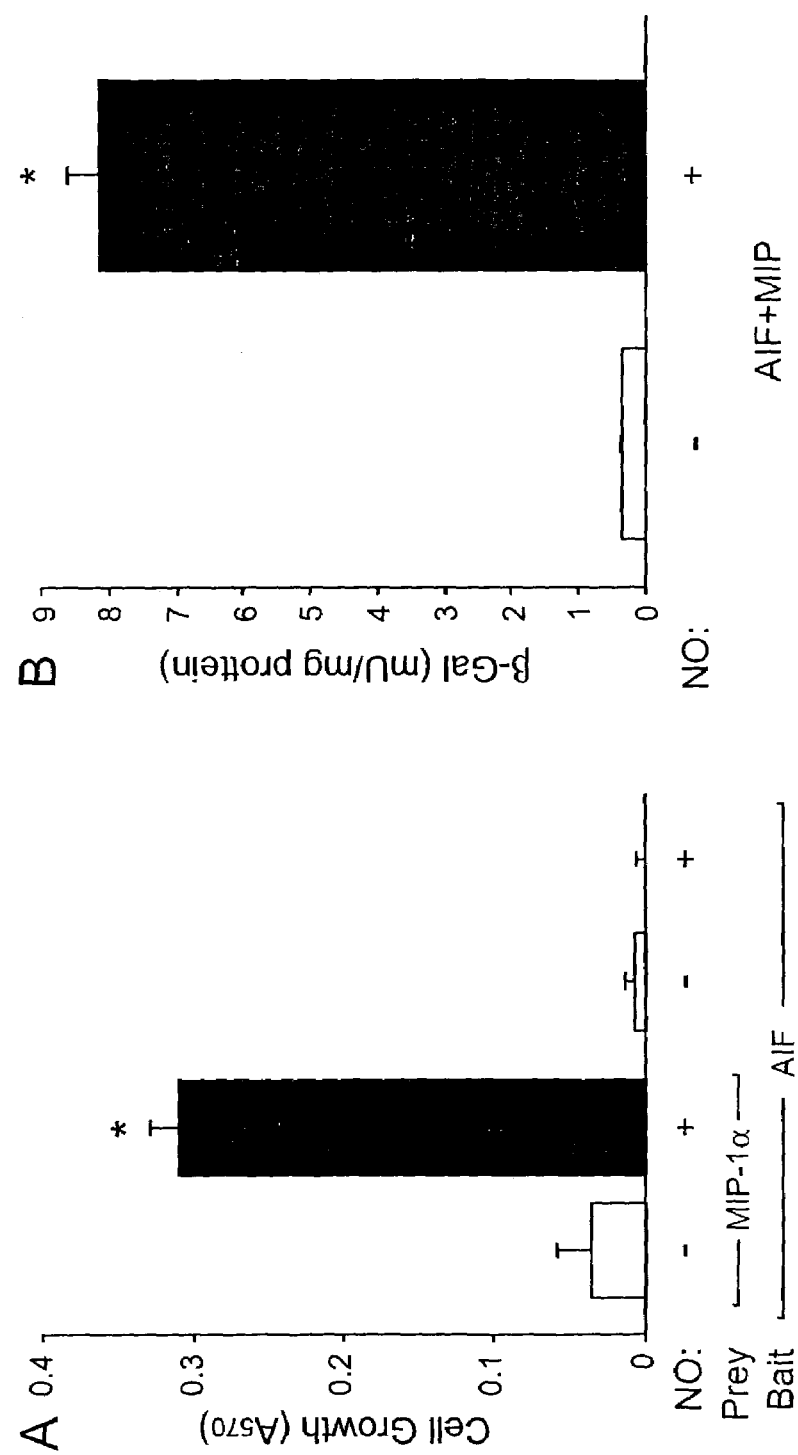

SEQUENCE LISTING

<160> NUMBER OF SEQ ID NOS: 1

<210> SEQ ID NO 1
<211> LENGTH: 19
<212> TYPE: DNA
<213> ORGANISM: Artificial
<220> FEATURE:
<223> OTHER INFORMATION: EcoRI Adapter

<400> SEQUENCE: 1
aattcgcggc cgcgtcgac                                                  19

PROTEOMIC SCREENING FOR REDOX STATE DEPENDENT PROTEIN—PROTEIN INTERACTIONS

RELATED APPLICATIONS

This application claims the benefit of PCT/US02/31571 filed Oct. 15, 2002. The contents of this application is incorporated herein by reference in its entirety.

FIELD OF THE INVENTION

This invention is directed to methods of identifying proteins involved in, or representing markers for, disease, drug reactions, neoplasm (tumor) or infection. This invention also relates to methods of identifying protein interactions and previously unknown receptors and ligands.

BACKGROUND OF THE INVENTION

Signal transduction is often coordinated by multi-protein complexes (Kumar and Snyder, 2002; Gavin et al., 2002; Ho et al., 2002). Constitutive interactions among proteins function in the initiation of signaling, while inducible or regulated protein-protein interactions are generally required for signal processing and propagation (Hunter, 2000). These dynamic interactions form the basis of complex regulatory circuits that determine biological function. Identifying the makeup of these circuits is a major challenge, however, because they involve multiple low affinity interactions that are controlled by dynamic post-translational protein modifications in response to multiple stimuli (Hunter, 2000; Zhu et al., 2001).

A number of non-covalent bonds form between proteins when two protein surfaces are precisely matched, and these bonds account for the specificity of recognition. Protein-protein interactions are involved in, for example, the assembly of enzyme subunits, antigen-antibody reactions, forming the supramolecular structures of ribosomes, filaments, and viruses in transport, and in the interaction of receptors on a cell with growth factors and hormones. Products of oncogenes can give rise to neoplastic transformation through protein-protein interactions. For example, some oncogenes encode protein kinases whose enzymatic activity on cellular target proteins leads to the cancerous state. Another example of a protein-protein interaction occurs when a virus infects a cell by recognizing a polypeptide receptor on the surface, and this interaction has been used to design antiviral agents.

Protein-protein interactions have been generally studied in the past using biochemical techniques such as crosslinking, co-immunoprecipitation and co-fractionation by chromatography. A disadvantage of these techniques is that interacting proteins often exist in very low abundance and are, therefore, difficult to detect. Another major disadvantage is that these biochemical techniques involve only the proteins, not the genes encoding them. When an interaction is detected using biochemical methods, the newly identified protein often must be painstakingly isolated and then sequenced to enable the gene encoding it to be obtained. Another disadvantage is that these methods do not immediately provide information about which domains of the interacting proteins are involved in the interaction. Also, small changes in the composition of the interacting proteins cannot be tested easily for their effect on the interaction.

A genetic system that is capable of rapidly detecting which proteins interact with a known protein, determining which domains of the proteins interact under physiological conditions, and providing the genes for the newly identified interacting proteins has only recently been made available. The yeast two-hybrid system currently represents the most powerful in vivo approach to screen for polypeptides that could bind to a given target protein and this invention provides a unique way of utilizing the two hybrid system for studying novel protein-protein interactions under physiological conditions.

The yeast two hybrid system described here is based on transcriptional activation. Transcription is the process by which RNA molecules are synthesized using a DNA template. Transcription is regulated by specific sequences in the DNA which indicate when and where RNA synthesis should begin. These sequences correspond to binding sites for proteins, designated transcription factors, which interact with the enzymatic machinery used for the RNA polymerization reaction.

In these systems, reconstitution into a hybrid caused by protein-protein interaction of a bait protein with a prey protein is monitored by activation of a reporter gene. Two-hybrid systems are discussed, for example, in Nandabalan et al U.S. Pat. No. 6,083,693; U.S. Pat. No. 5,283,173; U.S. Pat. No. 5,610,015; U.S. Pat. No. 5,634,463; U.S. Pat. No. 5,885,779; Klein et al. United States Statutory Invention Registration H1,892; LeGrain et al U.S. Pat. No. 6,187,535; and Rain, J.-C., et al. Nature 409, 211–215 (Jan. 11, 2001). The bait is a protein or proteins known to be involved in the pathophysiological process for which the determination is being made. The prey can be constituted of all proteins and genes expressed in cells of an affected tissue or body fluid or an election therefrom. Other methods of determining protein-protein interactions (e.g., as described in Zhu, H, et al., Science 293, 2101–2105 (2001) and as described below) can also be used. In general, the bait protein is derived from genomic DNA or a cDNA library. The cDNA library can be derived from a cell, for example, a macrophage, a cytokine activated macrophage, an endothelial cell, a muscle cell, a tumor cell or a kidney cell. Alternatively, the cDNA library can be derived from a cell treated with a drug, preferably a chemotherapeutic drug such as cisplatin.

In essence, the two putative protein partners are genetically fused to the DNA-binding domain of a transcription factor and to a transcriptional activation domain, respectively. A productive interaction between the two proteins of interest will bring the transcriptional activation domain into the proximity of the DNA-binding domain and will trigger directly the transcription of an adjacent reporter gene, for example, lacZ, giving a screenable phenotype. The transcription can be activated through the use of two functional domains of a transcription factor: a domain that recognizes and binds to a specific site on the DNA and a domain that is necessary for activation, as reported by Keegan et al. (1986) and Ma et al. (1987).

Transcriptional activation has been studied using the GAL4 protein of the yeast *Saccharomyces cerevisiae* (*S. cervisiae*). The GAL4 protein is a transcriptional activator required for the expression of genes encoding enzymes of galactose utilization, see Johnston, Microbiol. Rev., 51, 458–476 (1987). It consists of an N-terminal domain which binds to specific DNA sequences designated $UAS_G$, (UAS stands for upstream activation site, G indicates the galactose genes) and a C-terminal domain containing acidic regions, which is necessary to activate transcription, see Keegan et al. (1986), supra., and Ma and Ptashne. (1987), supra. As discussed by Keegan et al., the N-terminal domain binds to DNA in a sequence-specific manner but fails to activate transcription. The C-terminal domain cannot activate transcription because it fails to localize to the UAS$_G$, see for example, Brent and Ptashne, Cell, 43, 729–736 (1985). However, Ma and Ptashne have reported (Cell, 51, 113–119 (1987); Cell, 55, 443–446 (1988)) that when both the GAL4 N-terminal domain and C-terminal domain are fused together in the same protein, transcriptional activity is induced. Other proteins also function as transcriptional activators via the same mechanism. For example, the GCN4 protein of *Saccharomyces cerevisiae* as reported by Hope and Struhl, Cell, 46, 885–894 (1986), the ADR1 protein of *Saccharomyces cerevisiae* as reported by Thukral et al., Molecular and Cellular Biology, 9, 2360–2369, (1989) and the human estrogen receptor, as discussed by Kumar et al., Cell, 51, 941–951 (1987) both contain separable domains for DNA binding and for maximal transcriptional activation.

Recently, Rossi et al. (1997) described a different approach, a mammalian "two-hybrid" system, which uses β-galactosidase complementation (Ullmann et al., 1968) to monitor protein-protein interactions in intact eukaryotic cells. The number of genome sequences of prokaryotic as well as eukaryotic host organisms available is increasing exponentially and there is a great need for new tools directed to the functional and global study of these newly characterized complete or partial genomes.

Systems for determining protein-protein interactions which are useful herein are also described in Fung, E. T., et al, Current Opinion in Biotechnology 12:65–69 (2001) and Delneri, I., et al, Current Opinion in Biotechnology 12:87–91 (2001). Systems for determining protein interactions or activity include those described in Sakura, T., et al., Cell (1998), 573–585 and Hare, 1, et al., Nature Medicine, Vol 5, 1241–1242 (1999). These systems involve a search for an orphan receptor or ligand where readout is measured by changes in an intracellular second messenger such as calcium or G-protein activity. Other systems for determining protein interactions or activity include those described in Scherer, P., et al, Nature Biotechnology 16, 581–586 (1998). These systems involve a search for new epitopes that has been unmasked through protein-protein interaction.

Systems for determining changes in the level of protein expression are described in Fung, E. T., et al, Current Opinion in Biotechnology 12: 65–69 (2001). Systems for determining changes in the interaction between proteins and other molecules (e.g., DNA, RNA, lipids) are described in Ren, B., et al, Science 290, 2306 (2000) and in Marshall, H. and Stamler, J. S., Biochemistry 40, 1688 (2001). Methods for determining genomic interactions include methods for assaying the expression of genes in differential display, e.g., as described in Zohinhofer, D., et al., Circulation, 103, 1396–1402 (2001) and SAGE where levels of mRNA are quantified through hybridization or other means of quantification, e.g., as described in Zhang, L., et al., Science Vol. 276, 1268–1272 (1997).

Strategies for studying cellular function involved in disease states generally rely on comparison of control and disease states. A number of different proteomic and genomic strategies, including differential profiling platforms and functional assays (e.g., interaction studies) have been routinely employed for this purpose. These assays have long relied on the assumption that they accurately simulate the pathophysiological processes under investigation. However, they are carried out in "open" air and, therefore, are performed in the absence of specific and important protein modifications that are characteristic of physiological conditions, e.g., modifications that occur in the presence of nitric oxide (NO).

Nitric oxide (NO) is a ubiquitous molecule that propagates its signal through posttranslational nitrosylation of proteins (Stamler et al., 2001). Specifically, NO targets cysteine thiol and transition metal centers to regulate a broad functional spectrum of substrates, including all major classes of signaling proteins. An emerging theme in NO biology is that NO synthases (NOS) are localized within multi-protein signaling complexes where they regulate signal transduction (Stamler et al., 2001). But whether NO can directly affect protein-protein interactions transducing these signals, particularly in a disease state, has not been previously considered.

Accordingly, current screening methodologies lack a level of validation and biological significance because the actions and interactions identified using prior art methods are not causally related to the pathophysiological processes. It is therefore an object of the present invention to describe methods for identifying protein interactions under more physiological conditions. Specifically, this invention relates to the utilization of, for example, a modified yeast two-hybrid screening methodology in order to assess the possibility of NO-dependent regulation of protein-protein interactions in a cellular context.

BRIEF SUMMARY OF THE INVENTION

This invention provides novel methods for identifying protein interactions that are regulated by the redox state of the cell in which they occur and may, therefore, be regulated by a "redox state modifier molecule" (RSMM). In general, modification of the redox state will be any change of the redox state compared to normal physiological conditions. Specifically, this invention provides a method for identifying a protein complex whose formation is inhibited by an RSMM ("RSMM inhibited protein complex"); a method for identifying a protein complex whose formation is induced by an RSMM ("RSMM induced protein complex"); a method for identifying an agent capable of inhibiting RSMM induction of a protein complex; and a method for identifying an agent capable of inhibiting an RSMM inhibition of protein complex formation.

This invention provides a novel method for detecting an interaction between a first test protein and a second test protein in the presence of an RSMM. RSMMs are those compounds produced in vivo that are often characteristic of a pathophysiological process and which, because of their presence and/or concentration, affect a redox state. An RSMM is often produced in enzymatic reactions associated with pathophysiological processes. Specific RSMMs may be implicated in some diseases but not others. For example, certain oxidases are highly activated in inflammatory bowel disease, but not in atherosclerosis. A specific oxidase is responsible for bone resorption and another for hypertension. A certain diaphorase controls the activity of p53-dependent apoptotic death cascades (implicated in cancers) but is not implicated in other apoptotic mechanisms which are p53-independent. Nitric oxide synthase causes redox mediated damage in diabetes. Other enzymes involved in disease and other pathophysiological processes include oxygenases, peroxidases, reductases, transferases and dehydrogenases and the enzyme systems that control each of these kinds of enzymes.

This invention provides a genetically engineered and further modified two hybrid-based methodology to address the question of whether, for example, NO can regulate protein-protein interactions. It also provides a method of screening for these interactions under physiologically relevant conditions. This strategy has revealed multiple NO-dependent protein-protein interactions, including interactions of nitric oxide synthases (NOSs), whose physiological relevance is suggested by their occurrence and dependence on endogenous NO in mammalian cells. This invention thus shows that NOSs will regulate both their own target interactions and also those of other proteins within signaling assemblies. It is important to emphasize that current proteomic screens are performed in the absence of NO, whereas NO is ubiquitous in mammalian cells. Accordingly, broader application of the methods presented here should lead to the discovery of a large array of novel interactions, to new biological functions, and ultimately to a more accurate description of the human proteome.

Compounds contemplated for use in the invention include both reactive oxygen species (ROS) and reactive nitrogen species (RNS).

BRIEF DESCRIPTION OF THE DRAWINGS

FIG. 5 illustrates NO-dependent interaction of apoptosis inducing factor (AIF) with macrophage inflammatory protein-1 alpha (MIP-1α).

DETAILED DESCRIPTION OF THE INVENTION

Figure 1:
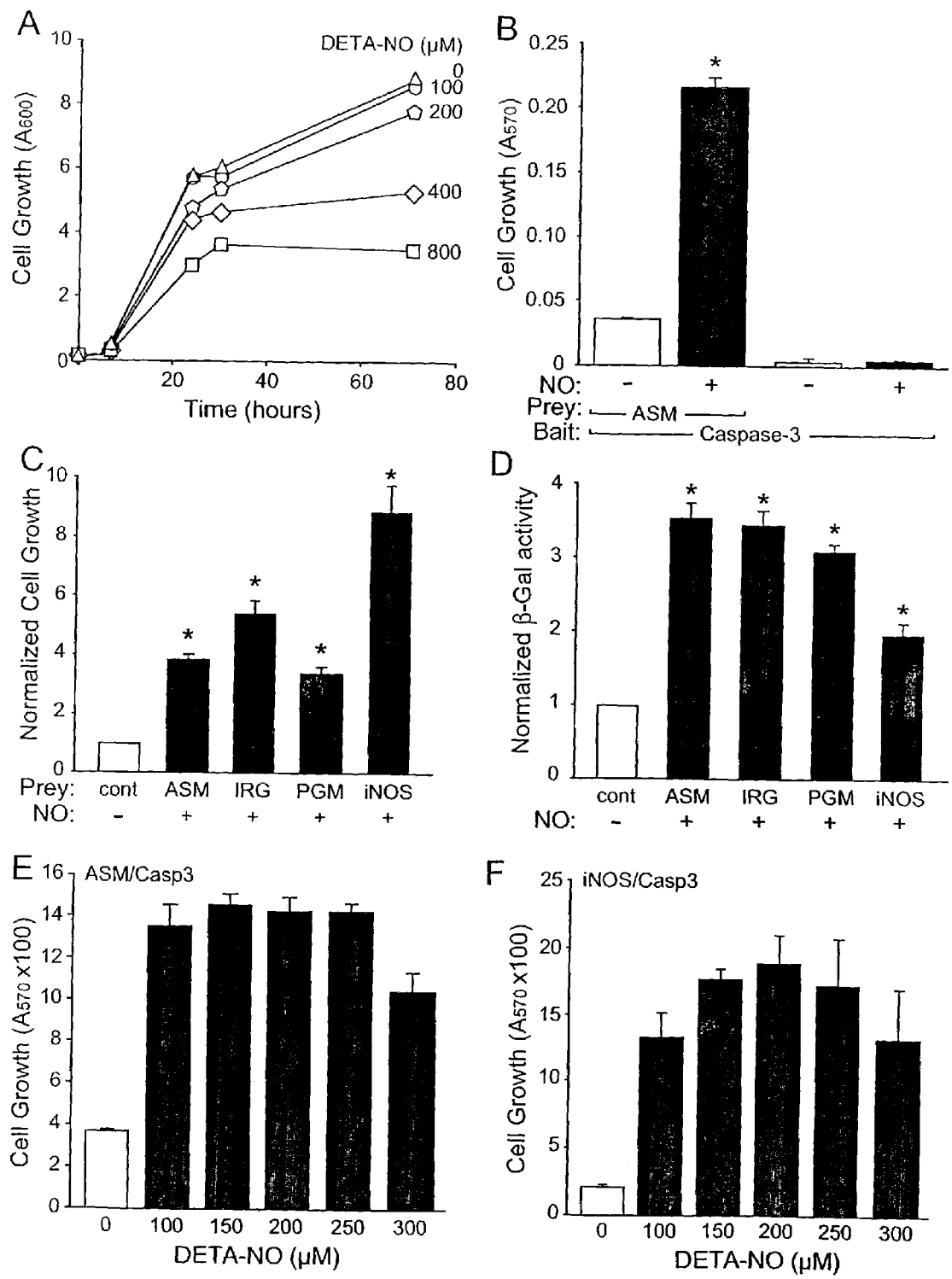
FIG. 1 illustrates NO-dependent interactions revealed in a modified yeast two-hybrid system.

As used herein, "protein" and "protein complex" are used synonymously with "polypeptide" and "polypeptide complex". A "purified" polypeptide, protein or biologically active portion thereof is substantially free of cellular material or other contaminating proteins from the cell or tissue source from which the polypeptide is derived, or substantially free from chemical precursors or other chemicals when chemically synthesized. The language "substantially free of cellular material" includes preparations of protein in which the protein is separated from cellular components of the cells from which it is isolated or recombinantly produced. In one embodiment, the language "substantially free of cellular material" includes preparations of polypeptide complex having less than about 30% (by dry weight) of non-complex proteins (also referred to herein as a "contaminating protein"), more preferably less than about 20% of contaminating protein, still more preferably less than about 10% of contaminating protein, and most preferably less than about 5% non-complex protein. When the polypeptide or complex is recombinantly produced, it is also preferably substantially free of culture medium, e.g., culture medium represents less than about 20%, more preferably less than about 10%, and most preferably less than about 5% of the volume of the protein preparation.

As used herein, the term "analogous protein complex" refers to the comparison of protein complexes between two different cells. A protein complex found in cell "A" would be analogous to a protein complex in cell "B" if the two protein complexes are identical. The "analogous protein complex" may be present to a lesser degree in cell "A" verses cell "B" or it may be present in cell "A" and not present in cell "B".

As used herein, the term "lesser degree" refers to the extent or measure of a difference in a protein complex between a first and second cell.

The term "antibody" as used herein refers to immunoglobulin molecules and immunologically active portions of immunoglobulin molecules, e.g., molecules that contain an antigen binding site that specifically binds (immunoreacts with) an antigen, such as a polypeptide complex. Such antibodies include, e.g., polyclonal, monoclonal, chimeric, single chain, Fab and F(ab')2 fragments, and an Fab expression library. In specific embodiments, antibodies are generated against human ortholog complexes.

The term "monoclonal antibody" or "monoclonal antibody composition", as used herein, refers to a population of antibody molecules that contain only one species of an antigen binding site capable of immunoreacting with a particular epitope of a polypeptide complex. A monoclonal antibody composition thus typically displays a single binding affinity for a particular protein with which it immunoreacts.

As used herein, "modulate" is meant to refer to an increase or decrease in the rate at which a complex is assembled or dissembled, or to increase or decrease the stability of an assembled complex. Thus, an agent can be tested for its ability to disrupt a complex, or to promote formation or stability of a complex.

As used herein, the term "derivative" or "derived" refers to a chemical substance, for example a truncated protein or peptide, related structurally to another substance and theoretically derivable from it.

As used herein, the term "region", as in protein region, refers to an indefinite number of amino acids in a defined area of a parent protein.

As used herein, the term "physiologically levels" refer to a characteristic of or appropriate to an organism's healthy or normal functioning. As used herein, the term "physiologically compatible" refers to a solution or substance, for example media, that can be utilized to mimic an organism's healthy or normal environment. For in vivo use, the physiological compatible solution may include pharmaceutically acceptable carriers, excipients, adjuvants, stabilizers, and vehicles. The composition may be in solid, liquid, gel, or aerosol form.

The terms "cell culture medium" and "culture medium" refer to a nutrient solution used for growing cells that typically provides at least one component from one or more of the following categories: 1) an energy source, usually in the form of a carbohydrate such as glucose; 2) all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally-occurring elements that are typically required at very low concentrations, usually in the micromolar range.

For mammalian cells, the cell culture medium is generally "serum free" when the medium is essentially free of serum from any mammalian source (e.g. fetal bovine serum (FBS)). By "essentially free" is meant that the cell culture medium comprises between about 0–5% serum, preferably between about 0–1% serum, and most preferably between about 0–0.1% serum. Advantageously, serum-free "defined" medium can be used, wherein the identity and concentration of each of the components in the medium is known (ie., an undefined component such as bovine pituitary extract (BPE) is not present in the culture medium).

As defined herein "specific binding" refers to the ability of two proteins, peptides or an antibody and antigen to interact.

As used herein, the term "disrupt" refers to the displacement of at least one polypeptide from a complex of at least two polypeptides.

As utilized herein, the term "pharmaceutically acceptable" means approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

As used herein "ROS" refers to, for example, hydrogen peroxide, superoxide, hypochlorite ion and hydroxyl radical.

As used herein, an "RNS" refers to, for example, nitric oxide or nitric dioxide. In a preferred embodiment, the RNS is nitric oxide and compounds that release nitric oxide or otherwise directly or indirectly deliver or transfer nitric oxide in vivo to a site of its activity, such as on a cell membrane.

As used here, the term "nitric oxide" encompasses uncharged nitric oxide (NO) and charged nitric oxide species, particularly including nitrosonium ion ($NO^+$) and nitroxyl ion ($NO^-$). The reactive form of nitric oxide can be provided by gaseous nitric oxide. Compounds having the structure X-NO wherein X is a nitric oxide releasing, delivering or transferring moiety, include any and all such compounds which provide nitric oxide to its intended site of action in a form active for their intended purpose.

As used herein, the term "nitric oxide adducts" encompasses any of such nitric oxide releasing, delivering or transferring compounds, including, for example, S-nitrosothiols, S-nitroso amino acids, S-nitroso-polypeptides, and nitrosoamines. It is contemplated that any or all of these "nitric oxide adducts" can be mono- or poly-nitrosylated at a variety of naturally susceptible or artificially provided binding sites for nitric oxide. In a preferred embodiment, the NO adduct is diethylenetriamine-NO (DETA-NO).

The headings for the subsequent sections are provided for organizational purpose only. They are not to be considered limiting.

Identification of Protein Interactions Regulated by Redox State Modifier Molecules This invention provides novel methods for identifying protein interactions that are regulated by the redox state of the cell in which they occur and may, therefore, be regulated by a "redox state modifier molecule" (RSMM). An RSMM is able to modify the redox state of a cell. In general, modification of redox state will be a change of the redox state as compared to normal physiological conditions. Specifically, this invention provides a method for identifying a protein complex whose formation is inhibited by an RSMM ("RSMM inhibited protein complex"); a method for identifying a protein complex whose formation is induced by an RSMM ("RSMM induced protein complex"); a method for identifying an agent capable of inhibiting RSMM induction of a protein complex; and a method for identifying an agent capable of inhibiting an RSMM inhibition of protein complex formation.

(a) RSMMs

In many cases, RSMMs and concentrations thereof associated with a particular pathophysiologic process are already known. For example, superoxide is associated with the classical model of 1-metal-4-phenyl-1,2,3,6-tetrahydropyridine (MPTP) induced Parkinson's disease and nitration is implicated in depletion of dopamine. Hypotensive shock is produced by NO generated by upregulation of nitric oxide synthase. Hyperglycemia (30 millimolar D-glucose) produces selective oxidative stress within the mitochondria. The source of this redox state modification is nitric oxide synthase and the molecule it produces in this case is superoxide.

Alterations of the concentrations of various physiological conditions can cause changes in redox states, which can lead to pathophysiological processes. For example, variations in glucose concentration have been linked to diabetes and ischemia reperfusion injury. pH variation is associated with mitochondria during apoptosis, with ischemic areas and with abscess or infected area. Where a pathophysiological process is not known to involve pH variation from non-pathophysiological state, this can be screened for by dyes or electrodes. Disorders are known which are associated with alteration of metal presence from normal. For example, acrodermatitis enteropathatica results from malabsorption of zinc, and Wilson's disease involves copper toxicosis. There is a secondary effect of redox state modification where the alteration of metal amount affects redox state. For example, copper ions are well known to participate in redox reactions and zinc and cadmium influence the redox state of cells, e.g., by chelating thiol.

Changes in redox states also involve the alteration of an NADH ratio. NADH concentration is altered, e.g., in the case of sleep disorders related to circadian rhythms. Alteration of NADH levels can be produced, for example, by knockout of lactate dehydrogenase (LDH), e.g., in yeast cells in a yeast two-hybrid determination.

This invention also provides methods of inducing novel protein-protein interactions as well as inhibiting an otherwise present protein-protein interaction. The term protein-protein interaction refers to any type of meaningful interaction that proteins are capable of (protein-RNA, receptor-ligand, etc.), and these interactions mediate most cellular processes. The strength of binding between two proteins is typically described by the dissociation constant ($K_d$) and can be determined by many methods. Generally, interacting polypeptides form heterodimers with a dissociation constant ($K_d$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$ or more, under suitable physiological conditions.

In one embodiment, endothelial cell mitochondrial protein-protein interactions are determined in the presence of superoxide generating systems, e.g., by adding an herbicide, such as paraquat, or by transfecting yeast with nitric oxide synthase and then adding paraquat.

In one embodiment, redox state conditions include physiological $pO_2$, physiological concentrations of NO, physiological levels of nitrosothiols, very low levels of reactive oxygen species, and reducing conditions.

The oxygen levels utilized are much lower than the current level, which is conventionally used, namely the concentration of oxygen in air, room air having a $pO_2$ of 150 mm Hg. The oxygen concentrations utilized are preferably those in the tissue or organ or blood perfusing through for the physiological process. This concentration varies widely. For example, alveolar $pO_2$ is 100 mm Hg, skeletal muscle $pO_2$ ranges from 10 to 30 mm Hg and exercising muscle is still lower and the $pO_2$ in the villus (a loop in the small intestine) is close to zero. Moreover, while physiological $pO_2$ is considered to be ~30 mm Hg, the $pO_2$ on running is ~5 mm Hg and rises above 30 mm Hg on abrupt stopping of running, and the $pO_2$ in the brain associated with thinking is 10–20 mm Hg. Thus, a range of oxygen concentrations are considered suitable for the physiological determination but the oxygen concentration used should be lower than that of room air and is preferably below 100 mm Hg. The physiological concentration of NO utilized is nanomolar to submicromolar concentration. In one embodiment, NO is utilized in a concentration of 10 nM to 1 µM. The physiological levels of nitrosothiols utilized range, for example, from 0.01 uM to 10 µM. The physiological levels of reactive oxygen species utilized range, for example, from $10^{-10}$ M to $10^{-6}$ M. Reducing conditions are also not present in conventional determinations which are carried out in room air. Reducing conditions can be provided, for example, by adding thiols or NAD(P)H, lowering $O_2$ concentration, adding chelating metals, adding physiological levels of ascorbate, e.g., to provide a concentration of 100 µM, or adding vitamin E. The appropriate redox state conditions can be effected by adding molecules to the experiment or by controlling the environment of the determination.

In another embodiment, the RSMM is produced by stimulation of an enzyme. The stimulation may be provided by addition of calcium/L-arginine, bradykinin, EGF or other cytokine, growth factor, neuroheumal, or developmental stimulus or activator of a G protein coupled receptor. The RSMM may be produced from an RSMM-generating enzyme. In one embodiment, the RSMM-generating enzyme is produced from a recombinant RSMM-generating enzyme vector. In a preferred embodiment, the RSMM-generating enzyme is NO synthase, NADPH oxidase, or a constitutively active rac G-protein.

RSMMs generated by enzymes include, for example, superoxide, peroxides (e.g., hydrogen peroxide), alkoxides, sulfoxides, brominating species, chlorinating species, nitrosating molecules (e.g., NO and RSNO where R is, for example, amino acid, peptide or protein), and nitrating molecules (e.g., peroxynitrite) and NO—generating molecules (e.g., Angeli's salt). These are generated relatively specifically in different diseases to different extents and/or in different subcellular compartments and the means exist to measure these with standard spectroscopic, immunological, electrochemical, chemical and photolytic approaches. Other RSMMs include enzymes that regulate glutathione, NADH and flavin levels and whose activities can be pharmacologically or genetically altered. Another important RSMM is $O_2$ in concentration in affected body tissue. Body tissue oxygen concentrations are much lower than the concentration of oxygen in air, room air having a $pO_2$ of 150 mm Hg. For example, tumors can have a $pO_2$ in the range of 10 mm Hg and a $pO_2$ in the case of oxygen induced reperfusion can be 80 mm Hg.

In a preferred embodiment, RSMMs are those compounds produced in vivo that are often characteristic of a pathophysiological process and which, because of their presence and/or concentration affect the redox state. In a more preferred embodiment the RSMM is a compound which directly affects the redox state. In a more preferred embodiment, the RSMM is selected from the group consisting of nitric oxide, nitric dioxide, dinitrogen trixide, dinitrogen tetraoxide, S-nitrosothiol, nitroxyl anion, HNO, nitrite, nitrate, C—, N, O, S or metal-nitroso or nitro compounds, hydrogen peroxide, peroxynitrite, other peroxides, alkoxides, superoxide, hypochlorite ion, hydroxyl radical and physiological $pO_2$.

In another preferred embodiment, the $pO_2$ is in a range from about 5 to about 100 mm Hg. In a more preferred embodiment, the range of $pO_2$ is from about 10 to about 50 mm Hg. In a most preferred embodiment, the range of $pO_2$ is from about 10 to about 30 mm Hg.

In another embodiment, the RSMM is an NO adduct. In one embodiment, the nitric oxide adducts are selected from the group of the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosated sugars, S-nitrosated-modified and unmodified oligonucleotides (preferably of at least 5, and more particularly 5–200, nucleotides); and an S-nitrosated hydrocarbon where the hydrocarbon can be a branched or unbranched, and saturated or unsaturated aliphatic hydrocarbon, or an aromatic hydrocarbon; S-nitroso hydrocarbons having one or more substituent groups in addition to the S-nitroso group; and heterocyclic compounds. S-nitrosothiols and the methods for preparing them are described in U.S. patent application Ser. No. 07/943,834, filed Sep. 14, 1992, Oae et al., Org. Prep. Proc. Int., 15(3):165–198, 1983; Loscalzo et al., J. Pharmacol. Exp. Ther., 249(3):726729, 1989, and Kowaluk et al., J. Pharmacol. E. Ther., 256:1256–1264, 1990, all of which are incorporated in their entirety by reference.

In a preferred embodiment, the NO adduct is selected from the group consisting of DETA-NO, S-nitrosothiol, SIN-1, angeli's salt, S-nitroso amino acids, S-nitrosopolypeptides, and nitrosoamines.

(b) RSMM Modified Media and Cell Culture

In one aspect, the invention provides a media for culturing a yeast cell comprising: (a) a physiologically compatible solution; and (b) at least one RSMM, in a concentration sufficient to modulate a redox reaction.

In yet another embodiment, the media is a liquid media. The media could be a semisolid media. In one embodiment, the media comprises between about 0.3% and about 10% of a solidifying agent. The solidifying agent could be agar or agarose. In a preferrerd embodiment, the media further comprises a substrate. In a preferred embodiment, the substrate is IPTG or ONPG. The media may also further comprise an inducer. In one embodiment, the inducer is X-gal. In another embodiment, the media is lyophilized. In yet another embodiment, the concentration of the RSMM is between 100 nM and 1 µM and the RSMM is present for a period of 24 hours. In a preferred embodiment, the yeast cell is *S. cervisiae*. In a further embodiment, the yeast cell does not express a functional flavohemoglobin gene.

This invention provides a method for culturing cells comprising: providing a media comprising an RSMM adduct; and culturing the cell in the media. In a preferred embodiment, the cell is a yeast cell lacking the flavohemoglobin gene. Flavohemoglobins are monomeric proteins containing one heme and one FAD as prosthetic groups and NADH as a co-factor. The primary sequence and the characterization of the protein are known for several prokaryotic and eukaryotic organisms. Flavohemoglobins act as NO denitrosylases, which convert NO and $O_2$ to $NO_3^-$. Therefore, by deleting the flavohemoglobin gene, the yeast are unable to consume NO.

In a preferred embodiment of the invention, the host cell is cultured in a media comprising a physiologically compatible solution; and at least one RSMM. The liquid media could be any broth or broth lyophilized into powders for example, LB broth, YT broth or NZY broth (Invitrogen Corporation, Carlsbad, Calif.). In other embodiments, the media is soft agar or solid agar.

In another aspect, the invention provides a method for culturing a cell in vitro comprising: (a) providing a media comprising at least one RSMM; and (b) culturing said cell in the media. In one embodiment, the RSMM is selected from the group consisting of nitric oxide, nitric dioxide, hydrogen peroxide, superoxide, hypochlorite ion, hydroxyl radical and physiological $pO_2$.

In one embodiment, the concentration of the RSMM is between 100 nM to 1 µM and the time is a period of 24 hours. In another embodiment, the media is a liquid media or a semisolid media. In a further embodiment, the media comprises between 0.3% to 10% of a solidifying agent. The solidifying agent may be agar or agarose.

(c) Methods (1) RSMM Induction and Inhibition of Protein-Protein Interactions

In one aspect, the invention provides a method for identifying an RSMM inhibited protein complex comprising: (a) culturing a first cell in a media comprising an RSMM; (b) culturing a second cell in a media without the RSMM; (c) identifying a first protein complex that exists in the second cell; (d) analyzing the first cell to determine the existence of a protein complex analogous to the first protein complex; wherein the RSMM inhibited protein complex is identified when the analogous protein complex does not exist or exists to a lesser degree than the first protein complex.

In another aspect, the invention provides a method for identifying an RSMM induced protein complex comprising: (a) culturing a first cell in a media comprising an RSMM; (b) culturing a second cell in a media without the RSMM; (c) identifying a first protein complex that exists in the first cell; (d) analyzing the second cell to determine the existence of a protein complex analogous to the first protein complex; wherein the RSMM induced protein complex is identified when the analogous protein complex does not exist or exists to a lesser degree than the first protein complex.

In another aspect, the invention includes a method for identifying an agent capable of inhibiting an RSMM induced protein complex comprising: (a) culturing a first cell in a media comprising an RSMM and a test agent; (b) culturing a second cell in a media without the RSMM; (c) analyzing the first cell to determine the existence of the RSMM induced protein complex; wherein the agent is identified when the RSMM induced protein complex does not exist or exists to a lesser degree than the protein complex that exists in the first cell in the absence of the test agent.

In one embodiment, the cell is a mammalian cell. In another embodiment, the cell is a hybrid cell. In a preferred embodiment, the hybrid cell is a yeast cell. In another embodiment, the protein complex includes at least one fusion protein. The fusion protein may be a protein fused to a detectable marker. In another embodiment, the protein complex includes a bait protein and a prey protein.

(2) Agents that Disrupt Protein-Protein Interactions

In another aspect, the invention provides a method of determining whether a first protein and a second protein interact in an environment comprising physiological levels of at least one RSMM, wherein the method comprises: (a) transfecting a host cell with a DNA construct expressing a first protein and a second protein to form a transfected host cell; (b) providing a media that comprises at least one RSMM; (c) culturing the transfected host cell to co-express the first and second proteins intracellularly; and (d) detecting whether between the first protein and the second protein interact.

The proteins for which the interactions are determined are any that are expressed in the physiological process and can be, for example, expressed in the kind of tissue that is affected by the pathophysiological process being compared to, and/or can be the same proteins (e.g., the same baits and preys). In a preferred embodiment, these proteins are cell death proteins and cell cycle proteins or derivatives thereof. In a preferred embodiment, proteins associated with a pathophysiological process include the NMDA receptor in stroke or caspase 3 in apoptosis.

In another aspect, the invention provides a method for identifying a compound capable of modulating a protein-protein interaction comprising: (a) providing a cell culture media containing at least one RSMM; (b) culturing a cell that expresses a first protein and a second protein in the cell culture media containing at least one RSMM, wherein an interaction between the first protein and second protein produces a first detectable signal; (c) contacting the cell with the compound wherein an interaction between the first protein and the second protein produces a second detectable signal, wherein the second detectable signal being lower than the first detectable signal is an indication that the compound is capable of modulating the interaction between the first and second protein.

In another aspect, the invention provides a method of detecting differences between a protein-protein interaction within a first cell and a second cell: (a) culturing the first cell in a media comprising an RSMM; (b) isolating a protein complex from the first cell; and (c) comparing the protein complex to a protein complex from the second cell grown in media without an RSMM. In one embodiment, the first cell and second cell are mammalian cells. In another embodiment, the isolating of the protein complex is by immunoprecipitation. The protein complex may comprise multiple members and at least one member is labeled with a detectable label. In one embodiment, the detectable label is selected from the group consisting of biotin, chemiluminescence, digoxigenin, fluorescence, iodination, kinase, ubiquitin and oligosaccharide.

In one embodiment, the interaction of proteins or protein regions is detected by a growth assay. In another embodiment, the cell culture media comprises an RSMM concentration of 1 nM to 1000 µM. The method may also further comprise the step of altering the concentration of the RSMM during culturing. In one embodiment, the alteration is an increase in the concentration of the RSMM. In another embodiment, the alteration is a decrease in the concentration of the RSMM. The RSMM may be administered at a physiological level. In one embodiment, there is more than one RSMM provided to the cell. In a preferred embodiment, at least one RSMM is nitric oxide. A growth assay can be performed by utilizing a calorimetric substrate in the media as well as an inducer of the substrate. In another embodiment, the media further comprises a calorimetric substrate, such as IPTG, and an inducer, such as Xgal. Both IPTG and Xgal are utilized for detection of lacZ transcription. LacZ is a bacterial gene used as a reporter construct for determination of transfection efficiency as well as histochemical localization following transfection of eukaryotic cells. The lacZ gene product β-galactosidase catalyzes the hydrolysis of the substrate X-gal to produce a blue color that is easily visualized with a microscope.

The invention also provides a method of detecting an interaction between a first protein and a second protein in an environment comprising physiological levels of at least one RSMM, the method comprising: (a) transfecting a host cell with a DNA construct expressing a first protein and a second protein to form a transfected host cell; (b) providing a media that comprises at least one RSMM; (c) culturing the transfected host cell to co-express the two proteins intracellularly; and (d) detecting an interaction of the two proteins.

The first protein and the second protein may be recombinantly expressed. In one embodiment, the first detectable signal or second detectable signal is detected by a calorimetric assay. In one embodiment, the first protein and the second protein are involved in cell death or cell growth. In another embodiment, the first protein and the second protein are cell division cycle proteins or derivatives thereof.

The invention also provides a method of identifying target proteins and/or genes in a disease specific manner comprising challenging cells involved in a disease with agent(s) to produce redox state-related modification of proteins and/or lipids that would subsequently mediate protein modification or provide interactions with proteins that are characteristic of the disease. For example, very low $pO_2$ is characteristic of a tumor.

The invention also provides a method of correlating protein interaction(s) with oxygen tension, comprising determining protein interaction(s) in the presence of oxygen tension different from that in room air, e.g., in the presence of oxygen tension less than 150 mm Hg.

In one embodiment, the method can be carried out using the conventional methods for determining protein-protein interactions, for example, two-hybrid systems, including yeast two-hybrid systems described above, except that the determinations are not carried out in room air but in the presence of oxygen tension less than that in room air, e.g., at $pO_2$ less than 150 mm Hg. In another embodiment, the oxygen tensions used preferably range from 0.1 mm Hg to 145 mm Hg, e.g., from 5 mm Hg to 100 mm Hg.

In another embodiment, the method can be carried out, for example, using high throughput screens for proteins, e.g., as described in Fung, E. T., et al. Current Opinion in Biotechnology 12, 65–69 (2001) and computer based bioinformatic approaches as described in Fung, E. T., et al, Current Opinion in Biotechnology 12, 65–69 (2001) in the presence of the agent(s) to produce redox state-related modifications of proteins and/or lipids that are characteristic of the disease, to identify specific RSMMs and specific protein and lipid related changes and thereby create redox maps of disease. Such maps can be used to create redox chips that are specific for diseases such as atherosclerosis or Alzheimer's disease where the samples used in conjunction with the chips can be DNA or RNA or protein material. The agent(s) to produce redox state related modifications are, for example, the RSMMs previously described. Preferably, the methods of the invention are carried out in the presence of oxygen concentration as determined in the tissue or organs affected by the disease or in blood perfusing said organs.

The invention also provides a method for screening a candidate compound for modulation of a protein-protein interaction comprising: (a) a cell culture media containing at least one RSMM, in an amount sufficient to modulate a redox reaction; (b) providing a cell that expresses a first and second protein wherein an interaction between the first and second protein produces a detectable signal in the presence of the RSMM; (c) contacting said cell with said candidate compound; and (d) detecting said signal to determine an effect of the compound on the protein interaction.

In a preferred embodiment, a plurality of determinations are carried out for each set of proteins, with different oxygen tensions being employed in each determination, e.g., using 5 or 10 different oxygen tensions where the oxygen tensions employed are in increments of 5 or 10 mm Hg.

This invention also provides a method of identifying a previously unknown receptor or orphan receptor or activating ligand, comprising measuring activation of receptor or orphan receptor in the presence of alteration of redox state of ligand. As previously indicated, general methods for identifying receptor, orphan receptor and activating ligand are described in Sakura, T., et al., Cell, 573–585 (1988) and Hare, J., et aL, Nature Medium, 5, 1241–1242 (1999). This class of method is modified in the invention herein by screening for receptor or orphan receptor or activating ligand by carrying out the identifying methods in a series of runs in the presence of a series of redox state modifications, whereby the receptor and activating ligand are associated with particular redox state modifications.

This invention also provides a method of determining epitopes involved in and/or representing markers of disease, comprising immunolabeling affected tissue or cells in the presence of redox state changes that are characteristic of the disease. General methodology useful in this method is described in Scherer, P., et al., Nature Biology 16, 581–586 (1998). The method of Scherer et al. is modified in the invention herein, in carrying out the determination in the presence of redox state modifications that are characteristic of the disease.

(3) Yeast Two-Hybrid Systems

In one embodiment, the cell is a yeast cell. In a preferred embodiment, the yeast cell is *S. cervisiae*. In yet another embodiment, the yeast cell does not express a functional flavohemoglobin gene.

In one aspect, the invention provides a method for detecting an interaction between a first test protein and a second test protein, the method comprising: (a) providing a yeast host cell comprising a detectable gene which expresses a detectable protein when the detectable gene is activated by a transcriptional activation domain when the transcriptional activation domain is in sufficient proximity to the detectable gene; (b) providing a first nucleic acid that encodes a first hybrid protein, the first hybrid protein comprising (i) a DNA-binding domain that recognizes a binding site in sufficient proximity to the detectable gene; and (ii) the first test protein; (c) providing a second nucleic acid encoding a second hybrid protein, the second hybrid protein comprising: (i) the transcriptional activation domain; and (ii) the second test protein; (d) introducing the first chimeric gene and the second chimeric gene into the host cell; (e) culturing said host cell in a media comprising an RSMM in an amount sufficient to modulate a redox reaction; (f) determining whether the detectable gene has been expressed, wherein expression of the detectable gene indicates an interaction between the first test protein and the second test protein.

In yet another embodiment, the DNA-binding domain and the transcriptional activation domain are derived from GAL4, GCN4 or ADR1.

The first nucleic acid or the second nucleic acid could be an insert from a genomic DNA or cDNA library. In one embodiment, the cDNA library is derived from a cell selected from the group consisting of a macrophage, a cytokine activated macrophage, an endothelial cell, a muscle cell or a tumor cell. In another embodiment, the cDNA library is derived from a cell treated with a drug. The drug may be a chemotherapeutic drug, for example, cisplatin. In another embodiment, the first hybrid protein and second hybrid protein are recombinantly expressed. In a preferred embodiment, the first test protein or second test protein is a prey protein. In another preferred embodiment, the first test protein or second test protein is a bait protein. In yet another embodiment, the expression of the detectable gene is visualized by a colorimetric assay. In one embodiment, the interaction of the first test protein and second test protein is determined by yeast two hybrid assay detection. In another embodiment, a growth assay is performed on the yeast host cell in the presence and absence of the RSMM. The first test protein and second test protein may be involved in cell death or cell growth. The first test protein and the second test protein may be cell division cycle proteins or derivatives thereof. In one embodiment, the yeast host cell is *S. cervisiae*. In another embodiment, the yeast host cell does not express a functional flavohemoglobin gene.

In another aspect, the invention provides a method for detecting an interaction between a first protein region and a second protein region comprising: (a) transfecting a yeast cell with a recombinant reporter gene coding for a detectable gene product; (b) transfecting the yeast cell with a first recombinant gene coding for a prey fusion protein, the prey fusion protein comprising a transcriptional enhancer domain and said first protein region; (c) transfecting the yeast cell with a second recombinant gene coding for a bait fusion protein, the bait fusion protein comprising a DNA-binding domain which binds a sequence on the reporter gene and the second protein region; and, (d) culturing the yeast cell in a media containing at least one RSMM in an amount sufficient to modulate a redox reaction, wherein reporter gene expression indicates the interaction between the first protein region and the second region.

In yet another embodiment, the DNA-binding domain and the transcriptional activation domain are derived from GAL4, GCN4 or ADR1. The prey fusion protein or the bait fusion protein may be encoded by an insert from a genomic DNA or cDNA library. In one embodiment, the cDNA library is derived from a cell selected from the group consisting of a macrophage, a cytokine activated macrophage, an endothelial cell, a muscle and a tumor cell. In another embodiment, the cDNA library is derived from a cell treated with a drug. In yet another embodiment, the drug is a chemotherapeutic drug, for example, cisplatin. The prey fusion protein and the bait fusion protein may be recombinantly expressed. The detectable gene product may be detected by a colorimetric assay. In another embodiment, a growth assay on the yeast cell is performed in the presence and absence of the RSMM. The first and second protein regions may be derived from proteins involved in cell death or cell growth. The first and second protein regions may be derived from cell division cycle proteins or derivatives thereof. In one embodiment, the yeast cell is *S. cervisiae*. In another embodiment, the yeast cell does not express a functional flavohemoglobin gene.

In one embodiment, the first protein and second protein may be recombinantly expressed. In one embodiment, the first protein or second protein is a prey protein. In a further embodiment, the first protein or second protein is a bait protein. The interaction between the first protein and second protein may be detected by a colorimetric assay or a yeast two hybrid assay. In another embodiment, this method further comprises performing a growth assay on the cell in the presence and absence of the RSMM. The first protein and second protein may be involved in cell death or cell growth. The first protein and second protein may be cell division cycle proteins or derivatives thereof.

(d) Purified Protein Complexes

In another aspect, the invention provides a purified complex comprising a first polypeptide and a second polypeptide, wherein the first polypeptide comprises an amino acid sequence selected from an apoptotic signaling molecule, wherein the second polypeptide comprises an amino acid sequence of the corresponding sequence selected from the group consisting of ASM, IRG, PGM-1, iNOS, nNOS and eNOS, and wherein the first polypeptide and the second polypeptide bind only in the presence of at least one RSMM. In one embodiment, the first polypeptide is selected from the group consisting of caspase-3, caspase-8, caspase-9, Apaf-1, Bcl-2 and AIF. The first polypeptide and second polypeptides may be labeled.

In one embodiment, the protein complex includes at least one fusion protein. The fusion protein may be a protein fused to a detectable marker. In another embodiment, the protein complex includes a bait protein and a prey protein.

In one aspect, the invention provides a purified complex comprising a first polypeptide and a second polypeptide, wherein the first polypeptide comprises a region of amino acids of an apoptotic signaling molecule, and wherein the second polypeptide comprises a region of amino acids of an interacting polypeptide selected from the group consisting of ASM, IRG, PGM-1, iNOS, nNOS and eNOS, and wherein the first polypeptide and the second polypeptide bind only in the presence of at least one RSMM. In one embodiment, the apoptotic signaling molecule is caspase-3, caspase-8, caspase-9, Apaf-1, Bcl-2 or AIF.

In another aspect, the invention provides a chimeric polypeptide comprising six or more amino acids of the first polypeptide of the previously described purified complex covalently linked to six or more amino acids of the second polypeptide of the previously described purified complex. In another aspect, the invention provides a nucleic acid encoding the chimeric polypeptide. In a further aspect, the invention provides a vector comprising the nucleic acid previously described. In yet another aspect, the invention provides a cell comprising the vector. In another aspect, the invention provides an antibody that specifically binds the purified complex. In one embodiment, the antibody specifically binds to the purified complex with a higher affinity than it binds to the first or second polypeptide when the polypeptides are not complexed.

This invention includes a purified complex that includes two or more polypeptides. In one embodiment, the invention provides purified complexes of two or more polypeptides. In a preferred embodiment, this complex is a redox associated polypeptide complex. As used herein, "a redox associated polypeptide complex" is meant to be a polypeptide complex that forms due to a redox state modification. One of the polypeptides includes a polypeptide selected from an apoptotic signaling peptide. In another embodiment, the first and second polypeptides are selected from the group consisting of caspase-3, caspase-8, caspase-9, Apaf-1, Bcl-2, AIF, ASM1, IRG, PGM-1, iNOS, nNOS and eNOS. In some embodiments a first polypeptide is listed as a "bait" polypeptide and a second polypeptide is denoted as "prey" polypeptide, while in other embodiments the first polypeptide corresponds to a "prey" polypeptide and the second is a "bait" polypeptide.

In certain embodiments, the first polypeptide is labeled. In other embodiments, the second polypeptide is labeled, while in some embodiments, both the first and second polypeptides are labeled. Labeling can be performed using any art-recognized method for labeling polypeptides. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes complexes of two or more polypeptides in which at least one of the polypeptides is present as a fragment of a complex-forming polypeptide according to the invention. For example, one or more polypeptides may include an amino acid sequence sufficient to bind to its corresponding polypeptide. A binding domain of a given first polypeptide can be any number of amino acids sufficient to specifically bind to, and complex with, the corresponding second polypeptide under conditions suitable for complex formation. The binding domain can be the minimal number of amino acids required to retain binding affinity, or may be a larger fragment or derivative of the polypeptides. Procedures for identifying binding domains can be readily identified by one of ordinary skill in the art and the procedures described herein. For example, nucleic acid sequences containing various portions of a "bait" protein can be tested in a yeast two hybrid screening assay in combination with a nucleic acid encoding the corresponding "prey" protein.

In other embodiments, the complexes are human ortholog complexes, chimeric complexes, or specific complexes implicated in microbial pathways.

This invention also provides novel complexes of NO-dependent interacting polypeptides which have not heretofore been shown to interact directly, as well as methods of using these complexes.

(e) Identification of Agents which Affect RSMMs

In another aspect, the invention provides a method of identifying an agent which disrupts a polypeptide complex, the method comprising: (a) providing the complex; (b) contacting the complex with a test agent; and (c) detecting the presence of a polypeptide displaced from the complex, wherein the presence of the displaced polypeptide indicates the agent disrupts the complex. In one embodiment, the agent is selected from the group consisting of a peptide, a small molecule, a soluble receptor, a receptor agonist and an antibody.

In another aspect, the invention provides a method for identifying an agent which disrupts a polypeptide complex comprising at least one apoptotic signaling protein or cell cycle protein, the method comprising: (a) providing the complex previously described; (b) contacting the complex with a test agent; and (c) detecting the presence of a polypeptide displaced from the complex, wherein the presence of displaced polypeptide indicates said agent disrupts the complex. In one embodiment, the agent is selected from the group consisting of a peptide, a small molecule, a soluble receptor, a receptor agonist and an antibody. In a further embodiment, the apoptotic signaling protein is selected from the group consisting of caspase-3, caspase-8, caspase-9, Apaf-1, Bcl-2 and AIF. In yet another embodiment, the cell cycle protein is selected from the group consisting of cyclin, phosphatase, kinase, oncogenic protein and tumor supressor protein.

In another aspect, the invention provides a method of identifying an agent which inhibits S-nitrosylation comprising: (a) culturing a first cell capable of S-nitrosylation in a media comprising a candidate inhibitor of S-nitrosylation; (b) culturing a second cell capable of S-nitrosylation in a media without the candidate inhibitor of S-nitrosylation wherein the second cell is similar to the first cell except for lacking the candidate inhibitor; and (c) comparing S-nitrosylation in both the first cell and the second cell wherein the agent which inhibits S-nitrosylation is identified when S-nitrosylation is less in the first cell than in the second cell. In one embodiment, the S-nitrosylation occurs at an S-nitrosylation consensus sequence. In a preferred embodiment, the S-nitrosylation consensus sequence is XCY, wherein X and Y are acidic and/or basic amino acids. In another preferred embodiment, wherein S-nitrosylation consensus sequence is KRHDE.

The invention further provides methods of identifying an agent which modulates the formation or stability of a redox associated polypeptide complex described herein.

In one embodiment, the invention provides a method of identifying an agent that promotes disruption of a redox associated polypeptide complex. The method includes providing a polypeptide complex, contacting the complex with a test agent, and detecting the presence of a polypeptide displaced from the complex. The presence of a displaced polypeptide indicates the disruption of the complex by the agent. In some embodiments, the complex contains at least one apoptotic signaling molecule. In another embodiment, the complex contains at least one cell cycle protein. Agents which disrupt complexes of the invention may present novel modulators of cell processes and pathways in which the complexes participate.

Any compound or other molecule (or mixture or aggregate thereof) can be used as a test agent. In some embodiments, the agent can be a small peptide, or other small molecule produced by e.g., combinatorial synthetic methods known in the art. In other embodiments, the agent can be a soluble receptor, receptor agonist or antibody. Disruption of the complex by the test agent, e.g. binding of the agent to the complex, can be determined using art recognized methods, e.g., detection of polypeptide using polypeptide-specific antibodies, as described above. Bound agents can alternatively be identified by comparing the relative electrophoretic mobility of complexes exposed to the test agent to the mobility of complexes that have not been exposed to the test agent.

Agents identified in the screening assays can be further tested for their ability to alter and/or modulate cellular functions, particularly those functions in which the complex has been implicated. These functions include, e.g., control of cell-cycle progression; regulation of transcription; or the control of intracellular signal transduction.

In another embodiment, the invention provides methods for inhibiting the interaction of a polypeptide with a ligand, by contacting a complex of the protein and the ligand with an agent that disrupts the complex, as described above. In certain embodiments, the polypeptides are apoptosis signaling proteins or cell cycle proteins. Inhibition of complex formation allows for modulation of cellular functions and pathways in which the targeted complexes participate.

Polypeptides of the Invention and Recombinant Techniques

Polypeptides forming the complexes according to the invention can be made using techniques known in the art. For example, one or more of the polypeptides in the complex can be chemically synthesized using art-recognized methods for polypeptide synthesis. These methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241–247 (1986); Barany, et al, *Intl. J. Peptide Protein Res.* 30:

705–739 (1987); Kent, *Ann. Rev. Biochem.* 57:957–989 (1988), and Kaiser, et al, *Science* 243: 187–198 (1989).

Alternatively, polypeptides can be made by expressing one or both polypeptides from a nucleic acid and allowing the complex to form from the expressed polypeptides. Any known nucleic acids that express the polypeptides, whether yeast or human (or chimerics of these polypeptides) can be used, as can vectors and cells expressing these polypeptides. Sequences of yeast ORFs and human polypeptides are publicly available, e.g. at the *Saccharomyces* Genome Database (SGD) and GenBank (see, e.g. Hudson et al., *Genome Res.* 7. 1169–1173 (1997). If desired, the complexes can then be recovered and isolated.

Recombinant cells expressing the polypeptide, or a fragment or derivative thereof, may be obtained using methods known in the art, and individual gene product or complex may be isolated and analyzed (See, e.g., as described in Sambrook et al., eds., MOLECULAR CLONING: A LABORATORY MANUAL, 2nd Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993). This is achieved by assays that are based upon the physical and/or functional properties of the protein or complex. The assays can include, e.g., radioactive labeling of one or more of the polypeptide complex components, followed by analysis by gel electrophoresis, immunoassay and cross-linking to marker-labeled products. Polypeptide complexes may be isolated and purified by standard methods known in the art (either from natural sources or recombinant host cells expressing the proteins/ protein complex). These methods can include, e.g., column chromatography (e.g., ion exchange, affinity, gel exclusion, reverse-phase, high pressure, fast protein liquid, etc), differential centrifugation, differential solubility, or similar methods used for the purification of proteins. In accordance with the present invention, several interactions have presently been identified where one of the interacting partners is an apoptotic signaling protein.

Inhibiting any of these interactions could lead to the disruption in cell proliferation or cell death.

As described above, certain embodiments of these complexes contain the binding domains of these polypeptides, while other embodiments contain conservative variants of these polypeptides.

In a further aspect, the invention provides a chimeric polypeptide that includes sequences of two interacting proteins according to the invention. The interacting proteins can be, e.g., the interacting protein pairs disclosed in the Examples section below. Also included are chimeric polypeptides including multimers, e.g., sequences from two or more pairs of interacting proteins. The chimeric polypeptide includes a region of a first protein covalently linked, e.g. via peptide bond, to a region of a second protein. In certain embodiments, the second protein is a species ortholog of the first protein. In the preferred embodiments, the chimeric polypeptide contains regions of first and second human proteins. In some embodiments, the chimeric polypeptide(s) of the complex include(s) six or more amino acids of a first protein covalently linked to six or more amino acids of a second protein. In other embodiments, the chimeric polypeptide includes at least one binding domain of a first or second protein.

Preferably, the chimeric polypeptide includes a region of amino acids of the first polypeptide able to bind to a second polypeptide. Alternatively, or in addition, the chimeric polypeptide includes a region of amino acids of the second polypeptide able to bind to the first polypeptide.

Nucleic acid encoding the chimeric polypeptide, as well as vectors and cells containing these nucleic acids, are within the scope of the present invention. The chimeric polypeptides can be constructed by expressing nucleic acids encoding chimeric polypeptides using recombinant methods, described above, then recovering the chimeric polypeptides, or by chemically synthesizing the chimeric polypeptides. Host-vector systems that can be used to express chimeric polypeptides include, e.g.: (i) mammalian cell systems which are infected with vaccinia virus, adenovirus; (ii) insect cell systems infected with baculovirus; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

The expression of the specific proteins may be controlled by any promoter/enhancer known in the art including, e.g.: (i) the SV40 early promoter (see e.g., Bemoist & Chambon, *Nature* 290: 304–310 (1981)); (ii) the promoter contained within the 3'-terminus long terminal repeat of Rous Sarcoma Virus (see e.g., Yamamoto, et al., *Cell* 22: 787–797 (1980)); (iii) the Herpesvirus thymidine kinase promoter (see e.g., Wagner, et al., *Proc. Natl. Acad. Sci. USA* 78: 1441–1445 (1981)); (iv) the regulatory sequences of the metallothionein gene (see e.g., Brinster, et al., *Nature* 296: 39–42 (1982)); (v) prokaryotic expression vectors such as the β-lactamase promoter (see e.g., Villa-Kamaroff, et al., *Proc. Natl. Acad. Sci. USA* 75: 3727–3731 (1978)); (vi) the tac promoter (see e.g., DeBoer, et al., *Proc. Natl. Acad. Sci. USA* 80: 21–25 (1983)).

Plant promoter/enhancer sequences within plant expression vectors may also be utilized including, e.g.,: (i) the nopaline synthetase promoter (see e.g., Herrar-Estrella, et al., *Nature* 303: 209–213 (1984)); (ii) the cauliflower mosaic virus 35S RNA promoter (see e.g., Garder, et al., *Nuc. Acids Res.* 9: 2871 (1981)) and (iii) the promoter of the photosynthetic enzyme ribulose bisphosphate carboxylase (see e.g., Herrera-Estrella, et al., *Nature* 310: 115–120 (1984)).

Promoter/enhancer elements from yeast and other fungi (e.g., the Gal4 promoter, the alcohol dehydrogenase promoter, the phosphoglycerol kinase promoter, the alkaline phosphatase promoter), as well as the following animal transcriptional control regions, which possess tissue specificity and have been used in transgenic animals, may be utilized in the production of proteins of the present invention.

Other animal transcriptional control sequences derived from animals include, e.g.,: (i) the insulin gene control region active within pancreatic β-cells (see e.g., Hanahan, et al., *Nature* 315: 115–122 (1985)); (ii) the immunoglobulin gene control region active within lymphoid cells (see e.g., Grosschedl, et al., *Cell* 38: 647–658 (1984)); (iii) the albumin gene control region active within liver (see e.g., Pinckert, et al., *Genes and Devel.* 1: 268–276 (1987)); (iv) the myelin basic protein gene control region active within brain oligodendrocyte cells (see e.g., Readhead, et al., *Cell* 48: 703–712 (1987)); and (v) the gonadotrophin-releasing hormone gene control region active within the hypothalamus (see e.g., Mason, et al., *Science* 234: 1372–1378 (1986)).

The vector may include a promoter operably-linked to nucleic acid sequences which encode a chimeric polypeptide, one or more origins of replication, and optionally, one or more selectable markers (e.g., an antibiotic resistance gene). A host cell strain may be selected which modulates the expression of chimeric sequences, or modifies/processes the expressed proteins in a desired manner. Moreover, different host cells possess characteristic and specific mechanisms for the translational and posttranslational processing and modification (e.g., glycosylation, phosphorylation, and the like) of expressed proteins. Appropriate cell lines or host systems may thus be chosen to ensure the desired modification and processing of the foreign protein is achieved. For example, protein expression within a bacterial system can be used to produce an unglycosylated core protein; whereas expression within mammalian cells ensures "native" glycosylation of a heterologous protein.

Antibodies

The invention further provides antibodies and antibody fragments (such as Fab or F(ab')2 fragments) that bind specifically to the complexes described herein. By "specifically binds" is meant an antibody that recognizes and binds to a particular polypeptide complex of the invention, but which does not substantially recognize or bind to other molecules in a sample, or to any of the polypeptides of the complex when those polypeptides are not complexed.

For example, a purified complex, or a portion, variant, or fragment thereof, can be used as an immunogen to generate antibodies that specifically bind the complex using standard techniques for polyclonal and monoclonal antibody preparation.

A full-length polypeptide complex can be used, if desired. Alternatively, the invention provides antigenic fragments of polypeptide complexes for use as immunogens. In some embodiments, the antigenic complex fragment includes at least 6, 8, 10, 15, 20, or 30 or more amino acid residues of a polypeptide. In one embodiment, epitopes encompassed by the antigenic peptide include the binding domains of the polypeptides, or are located on the surface of the protein, e.g., hydrophilic regions.

If desired, peptides containing antigenic regions can be selected using hydropathy plots showing regions of hydrophilicity and hydrophobicity. These plots may be generated by any method well known in the art, including, for example, the Kyte Doolittle or the Hopp Woods methods, either with or without Fourier transformation. See, e.g., Hopp and Woods, *Proc. Nat. Acad. Sci. USA* 78:3824–3828 (1981); Kyte and Doolittle, *J. Mol. Biol.* 157:105–142 (1982).

Various procedures known within the art may be used for the production of polyclonal or monoclonal antibodies. For example, for the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, a recombinantly expressed polypeptide complex. Alternatively, the immunogenic polypeptides or complex may be chemically synthesized, as previously discussed. The preparation can further include an adjuvant. Various adjuvants used to increase the immunological response include, e.g., Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against the complex can be isolated from the mammal (e.g., from the blood) and further purified by well known techniques, such as protein A chromatography to obtain the IgG fraction.

For preparation of monoclonal antibodies directed towards a particular complex, or polypeptide, any technique that provides for the production of antibody molecules by continuous cell line culture may be utilized. Such techniques include, e.g., the hybridoma technique (see Kohler & Milstein, *Nature* 256. 495–497 (1975)); the trioma technique; the human B-cell hybridoma technique (see Kozbor, et al., *Immunol Today* 4: 72 (1983)); and the EBV hybridoma technique to produce human monoclonal antibodies (see Cole, et al., In: *Monoclonal Antibodies and Cancer Therapy*, Alan R. Liss, Inc., (1985) pp. 77–96). If desired, human monoclonal antibodies may be prepared by using human hybridomas (see Cote, et al., *Proc. Natl. Acad. Sci. USA* 80: 2026–2030 (1983)) or by transforming human B-cells with Epstein Barr Virus in vitro (see Cole, et al., In: *Monoclonal Antibodies and Cancer Therapy*, supra).

Methods can be adapted for the construction of Fab expression libraries (see e.g., Huse, et al., *Science* 246: 1275–1281 (1989)) to allow rapid and effective identification of monoclonal Fab fragments with the desired specificity for the desired protein or derivatives, fragments, analogs or homologs thereof. Non-human antibodies can be "humanized" by techniques well known in the art. See e.g., U.S. Pat. No. 5,225,539. Antibody fragments that contain the idiotypes to a polypeptide or polypeptide complex may be produced by techniques known in the art including, e.g.: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) $F_v$ fragments.

Chimeric and humanized monoclonal antibodies against the polypeptide complexes, or polypeptides, described herein are also within the scope of the invention, and can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., *Science* 240: 1041–1043 (1988); Liu et al., *Proc. Nat. Acad. Sci. USA* 84: 3439–3443 (1987); Liu et al., *J. Immunol.* 139: 3521–3526 (1987); Sun et al., *Proc. Nat. Acad. Sci. USA* 84: 214–218 (1987); Nishimura et al., *Cancer Res.* 47: 999–1005 (1987); Wood et al., *Nature* 314: 446–449 (1985); Shaw et al., *J. Natl. Cancer Inst.* 80: 1553–1559 (1988); Morrison, *Science* 229: 1202–1207 (1985); Oi et al., *BioTechniques* 4: 214 (1986); U.S. Pat. No. 5,225,539; Jones et al., *Nature* 321: 552–525 (1986); Verhoeyan et al., *Science* 239: 1534 (1988); and Beidler et al., *J. Immunol.* 141: 4053–4060 (1988).

Methods for the screening of antibodies that possess the desired specificity include, e.g., enzyme-linked immunosorbent assay (ELISA) and other immunologically-mediated techniques known within the art. For example, selection of antibodies that are specific to a particular domain of a polypeptide complex is facilitated by generation of hybridomas that bind to the complex, or fragment thereof, possessing such a domain.

In certain embodiments of the invention, antibodies specific for the polypeptide complexes described herein may be used in various methods, such as detection of complex, and identification of agents which disrupt complexes. These methods are described in more detail, below. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Polypeptide complex-specific, or polypeptide-specific antibodies, can also be used to isolate complexes using standard techniques, such as affinity chromatography or immunoprecipitation. Thus, the antibodies disclosed herein can facilitate the purification of specific polypeptide complexes from cells, as well as recombinantly produced complexes expressed in host cells.

Pharmaceutical Compositions, Therapeutic or Diagnostic Uses and Kits

The invention further provides pharmaceutical compositions of purified complexes suitable for administration to a subject, most preferably, a human, in the treatment of disorders involving altered levels of such complexes. Such preparations include a therapeutically-effective amount of a complex, and a pharmaceutically acceptable carrier.

The therapeutic amount of a complex which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. However, suitable dosage ranges for intravenous administration of the complexes of the present invention are generally about 20–500 micrograms (µg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

Various delivery systems are known and can be used to administer a pharmaceutical preparation of a complex of the invention including, e.g.: (i) encapsulation in liposomes, microparticles, microcapsules; (ii) recombinant cells capable of expressing the polypeptides of the complex; (iii) receptor-mediated endocytosis (see, e.g., Wu et al., *J. Biol. Chem.* 262: 4429–4432 (1987)); (iv) construction of a nucleic acid encoding the polypeptides of the complex as part of a retroviral or other vector, and the like.

Methods of administration include, e.g., intradermal, intramuscular, intraperitoneal, intravenous, subcutaneous, intranasal, epidural, and oral routes. The pharmaceutical preparations of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the pharmaceutical preparation into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the pharmaceutical preparation locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or preneoplastic tissue.

Alternatively, pharmaceutical preparations of the invention may be delivered in a vesicle, in particular a liposome, (see, e.g., Langer, *Science* 249:1527–1533 (1990)) or via a controlled release system including, e.g., a delivery pump (see, e.g., Saudek, et al, *New Engl. J. Med.* 321: 574 (1989) and a semi-permeable polymeric material (see, e.g., Howard, et al., *J. Neurosurg.* 71: 105 (1989)). Additionally, the controlled release system can be placed in proximity of the therapeutic target (e.g., the brain), thus requiring only a fraction of the systemic dose. See, e.g., Goodson, In: *Medical Applications of Controlled Release,* 1984 (CRC Press, Bocca Raton, Fla.).

In another embodiment, the invention provides a method for identifying a polypeptide complex in a subject. The method includes the steps of providing a biological sample from the subject, detecting, if present, the level of polypeptide complex. In some embodiments, the complex includes a first polypeptide (a "bait" polypeptide) and a second polypeptide ("prey" polypeptide) selected. Any suitable biological sample potentially containing the complex may be employed, e.g. blood, urine, cerebral-spinal fluid, plasma, etc. Complexes may be detected by, e.g., using complex-specific antibodies as described above. The method provides for diagnostic screening, including in the clinical setting, using, e.g., the kits described above.

In still another embodiment, the present invention provides methods for detecting a polypeptide in a biological sample, by providing a biological sample containing the polypeptide, contacting the sample with a corresponding polypeptide to form a complex under suitable conditions, and detecting the presence of the complex. A complex will form if the sample does, indeed, contain the first polypeptide. In some embodiments, the polypeptide being detecting is a "prey" protein selected from the polypeptides caspase-3, caspase-8, caspase-9, Apaf-1, Bcl-2 and AIF, and is detected by complexing with the corresponding "bait" protein, such as, ASM, IRG, PGM-1, iNOS, nNOS and eNOS. Conversely, in other embodiments the polypeptide being detected is the "bait" protein. Alternatively, a yeast "bait" or "prey" ortholog may be employed to form a chimeric complex with the polypeptide in the biological sample.

In still another embodiment, the invention provides methods for removing a first polypeptide from a biological sample by contacting the biological sample with the corresponding second peptide to form a complex under conditions suitable for such formation. The complex is then removed from the sample, effectively removing the first polypeptide. As with the methods of detecting polypeptide described above, the polypeptide being removed may be either a "bait" or "prey" protein, and the second corresponding polypeptide used to remove it may be either a yeast or human ortholog polypeptide.

Methods of determining altered expression of a polypeptide in a subject, e.g. for diagnostic purposes, are also provided by the invention. Altered expression of proteins involved in cell processes and pathways can lead to deleterious effects in the subject. Altered expression of a polypeptide in a given pathway leads to altered formation of complexes which include the polypeptide, hence providing a means for indirect detection of the polypeptide level. The method involves providing a biological sample from a subject, measuring the level of a polypeptide complex of the invention in the sample, and comparing the level to the level of complex in a reference sample having known polypeptide expression. A higher or lower complex level in the sample versus the reference indicates altered expression of either of the polypeptides that forms the complex. The detection of altered expression of a polypeptide can be use to diagnose a given disease state, and or used to identify a subject with a predisposition for a disease state. Any suitable reference sample may be employed, but preferably the test sample and the reference sample are derived from the same medium, e.g. both are urine, etc. The reference sample should be suitably representative of the level polypeptide expressed in a control population.

The invention further provides methods for treating or preventing a disease or disorder involving altered levels of a redox associated polypeptide complex, or polypeptide, disclosed herein, by administering to a subject a therapeutically-effective amount of at least one molecule that modulates the function of the complex. As discussed above, altered levels of polypeptide complexes described herein may be implicated in disease states resulting from a deviation in normal function of the pathway in which a complex is implicated. In subjects with a deleteriously high level of complex, modulation may consist, for example, by administering an agent which disrupts the complex, or an agent which does not disrupt, but down-regulates, the functional activity of the complex. Alternatively, modulation in subjects with a deleteriously low level of complex may be achieved by pharmaceutical administration of complex, constituent polypeptide, or an agent which up-regulates the functional activity of complex. Pharmaceutical preparations suitable for administration of complex are described above.

The invention also provides a kit to perform the modified two hybrid assay. The kit contains a first vector which contains a first chimeric gene. This chimeric gene includes a promoter, transcription termination signal and a DNA binding domain. The kit also includes a second vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding the second test protein or protein fragment into the vector, in such a manner that the second test protein is capable of being expressed as part of a hybrid protein with the transcriptional activation domain. Preferably, the DNA-binding domain of the first hybrid protein and the transcriptional activation domain of the second hybrid protein are derived from transcriptional activators having separate DNA-binding and transcriptional activation domains. These separate DNA-binding and transcriptional activation domains are known to be found in the yeast GAL4 protein and are also known to be found in the yeast GCN4 and ADR1 proteins. Many other proteins involved in transcription also have separable binding and transcriptional activation domains which make them useful for the present invention. In another embodiment, the DNA binding domain and the transcriptional activation domain may be from different transcriptional activators. The second hybrid protein may be encoded on a library of plasmids that contain genomic, cDNA or synthetically generated DNA sequences fused to the DNA sequence encoding the transcriptional activation domain.

The second vector further includes a means for replicating itself in the host cell and in bacteria. The second vector also includes a second marker gene, the expression of which in the host cell permits selection of cells containing the second marker gene from cells that do not contain the second marker gene.

The kit includes a host cell, preferably a yeast strain of *Saccharomyces cerevisiae* or *Schizosaccharomyces pombe*. The host cell contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene. The host cell, by itself, is incapable of expressing a protein having a function of the first marker gene, the second marker gene, the DNA-binding domain, or the transcriptional activation domain.

Accordingly in using the kit, the interaction of the first test protein and the second test protein in the host cell causes a measurably greater expression of the detectable gene than when the DNA-binding domain and the transcriptional activation domain are present, in the absence of an interaction between the first test protein and the second test protein. The detectable gene may encode an enzyme or other product that can be readily measured. Such measurable activity may include the ability of the cell to grow only when the marker gene is transcribed, or the presence of detectable enzyme activity only when the marker gene is transcribed. Various other markers are well known within the skill of workers in the art.

The cells containing the two hybrid proteins are incubated in an appropriate media, which is optionally supplied with the kit, and the culture is monitored for the measurable activity. A positive test for this activity is an indication that the first test protein and the second test protein have interacted. Such interaction brings their respective DNA-binding and transcriptional activation domains into sufficiently close proximity to cause transcription of the marker gene.

In a specific embodiment, the invention provides kits containing a reagent, for example, an antibody described above, which can specifically detect a polypeptide complex, or a constituent polypeptide, described herein. Such kits can contain, for example, reaction vessels, reagents for detecting complex in sample, and reagents for development of detected complex, e.g. a secondary antibody coupled to a detectable marker. The label incorporated into the anti-complex, or anti-polypeptide antibody may include, e.g., a chemiluminescent, enzymatic, fluorescent, colorimetric or radioactive moiety. Kits of the present invention may be employed in diagnostic and/or clinical screening assays.

Other features of the invention will become apparent in the course of the following description of exemplary embodiments which are given for illustration of the invention and are not intended to be limiting thereof. All references, patents and patent applications cited are hereby incorporated by reference in their entirety.

EXAMPLES

Example 1

Yeast Two-Hybrid Screening

Methods:

Generation of Bait Plasmids

Construction of bait plasmids. A NcoI and XhoI digest of caspase-3 (Mannick et al., 1999) was integrated into pAS2-1 (Clontech). The entire open reading frame of AIF was derived from I.M.A.G.E. clones 1520292 and 25192, and sub-cloned into pAS2-1 (between NdeI and EcoRI sites). DNA sequencing confirmed construct identities, and the expression of bait proteins (fused to binding domains (BD)) was verified by immunobloting with BD and/or bait-specific monoclonal antibodies.

Modified Yeast

The YHB1 gene was deleted from yeast strain CG-1945 and the absence of NO consumption activity was verified (Liu et al., 2000). Yeast two-hybrid screening was then performed in the CG-1945-Δyhb1 host. Cells were sequentially transformed with bait (selection in tryptophan (Trp)-deficient medium) and library (selection in Trp-leucine (Leu)-deficient medium) plasmids according to published directions (P. L. Bartel, S. Fields, *The Yeast Two-Hybrid System*. A. Jacobson, Ed., Advances in Molecular Biology (Oxford University Press, New York, 1997). Cells containing pairs of interacting proteins were selected by their growth on histidine (His)-deficient medium and by expression of β-galactosidase (β-gal) activity.

Preparation of cDNA Library

Poly(A)$^+$ mRNA was purified from RAW264.7 cells stimulated with murine IFN-γ (100 units/ml) and bacterial LPS (100 ng/ml) for 0, 2, 4, 6, 8, 12, 18 and 24 hrs. The cDNAs were prepared using oligo(dT) and random primers, ligated to the EcoRI adaptor (5'-AATTCGCGGCCGCGTCGAC-3' SEQ ID NO:1) and cloned into the EcoRI site of pGAD10 (Clontech) prey plasmids. The average insert size was 1.7 kbp and the range of insert size was 0.4~3.5 kbp. The resultant library was amplified once in *E. coli* to obtain the plasmid cDNA library used for screening.

Yeast Two Hybrid Assay

Yeast (Δyhb1) were transformed with Gal4 BD-caspase-3 plasmid (bait) and a cDNA library (Gal4 AD prey plasmids) derived from activated (NO generating) macrophages. Screening was performed as described in the methods below. DETA-NO at less than 300 μM generates NO without inhibiting yeast growth (monitored by absorbance at 600 nm). Steady state NO concentrations are maintained at ~100 nM–1 μM range for several days as measured with an NO electrode (not shown).

Method 1:

Auxotrophic selection was carried out on agar plates (15 cm in diameter) enriched in 50 mM phosphate buffer (pH 7.2; His-Trp-Leu (triple)-deficient buffered medium (TDBM)). Yeast were cultured for 4 days at 30° C. in the presence or absence of DETA-NO (40 μl of a 0.3M solution). Clones that showed at least 3-fold greater growth in DETA-NO were selected and further analyzed for β-gal activity with ONPG (O-nitrophenyl β-D-galactopyranoside) as substrate. Prey plasmids were isolated from positive yeast clones and then re-introduced into the bait strain to confirm bait-prey interactions.

Method 2:

After cells were seeded on 1.5% agar they were covered with 3% low melting point agar, which in turn was layered with culture medium. NO donors (e.g. DETA-NO; 300 μM final concentration) were added to the liquid layer every 24 hours. Colonies are grown for 4 days as described in ref 9.

Method 3:

Auxotrophic selection was carried out in TDBM. Transformation with the cDNA library was followed by overnight growth in medium deficient in tryptophan and leucine. Transformants were then grown for 3 days in His-deficient medium supplemented with DETA-NO (typically 200 μM final concentration). The plasmid DNA was harvested and transformed into *E. Coli*. Individual clones were isolated, retransformed into bait strains, and reassessed for NO-dependent growth.

NO-Dependent Cell Growth of the ASM/Caspase-3 Clone

Cells were grown in His-Trp-Leu-deficient medium for 72 hrs with or without 200 μM DETA-NO (NO). As indicated by an asterisk (FIG. 1B), P<0.001 for ASM/Casp-3 without NO vs. all other comparisons (n=6).

NO-Dependent Interactions between Caspase-3 and a Set of Novel Partner Proteins (prey): ASM, IRG, PGM and iNOS Interactions are revealed as NO-dependent cell growth (FIG. 1C) (single asterisk, P<0.001 vs. NO-free control, n=6) and as increases in β-galactosidase activity (FIG. 1D) (single asterisk, P<0.004 vs. NO-free control, n=4). (FIG. 1E) Effect of NO concentration on growth of the ASM/caspase-3 clone. Cells were cultured in triple-deficient medium for 72 hrs (n=6). (FIG. 1F) Effect of NO concentration on growth of the iNOS/caspase-3 clone (culture conditions as in E)(n=6).

Macrophages exposed to cytokines (tumor necrosis factor and interleukin-I), a well-established model injury that is apoptotic in nature, were used.

Potential redox state-related modifier molecules were determined as being nitric oxide, superoxide and hydrogen peroxide, on the basis that these were detected as being produced in high levels in macrophages exposed to cytokines.

It was then established that nitric oxide but not superoxide or hydrogen peroxide is causal to cell injury by demonstration that inhibitors of nitric oxide protected the cells but inhibitors of superoxide or hydrogen peroxide did not.

It was then determined that nitric oxide, in addition to causing cell injury, also inhibited proteins involved in protection against cytokines. This result indicates that non-specific binding of nitric oxide is likely to have some deleterious consequences. Many-fold increased levels of S-nitrosothiol proteins were measured. This indicates that what is needed is a way to identify the S-nitrosylated proteins that are the targets of nitric oxide and/or the functional consequences of these modifications, so these modification can be manipulated without inhibiting proteins that protect against cytokines. Thus, the goal is to identify the S-nitrosylated proteins that are the targets of nitric oxide and/or the functional consequences of modifications mediated thereby.

For this purpose, protein-protein interactions were determined in a yeast two-hybrid system by the method described in Uetz, P., et al., Nature 403, 623–627 (2000) and Ito, T., et al., PNAS, 97, 1143–1147 (2000). The baits were all known proteins involved in apoptotic cascades. The preys were a library of macrophage genes (mRNA) expressed in response to cytokines that induce apoptosis. Mating pairs or transfectants were exposed to continuous nitric oxide presence at levels and flux rates mimicking those which are generated in macrophages, over 18 hours (the time course, over which apoptosis occurs in these cells). Room air was used in the determinations to mimic the cell condition at first and subsequently low $pO_2$ (about 5 mm Hg) was used to improve specificity and increase yield. New partners and/or inhibition of partners that were otherwise present, were sought. When caspase was used as a bait, it was found that nitric oxide induced a novel apoptosis-inducing interaction (based on sequence of the interacting protein) thus revealing a new and specific approach to inhibiting apoptosis (e.g., drugs that would inhibit interaction between caspase and the new protein). When a second protein was used, nitric oxide induced an interaction with a different protein. Use of other baits resulted in determination of further interactions.

A comparison between a physiological process using the same baits and preys in a yeast two-hybrid system using the redox state conditions, room air, nanomolar to submicromolar concentration of nitric oxide, nanomolar to micromolar level of nitrosothiols, no reactive oxygen species and reducing conditions provided by glutathione and NADH.

In all, 18 new targets were identified in response to nitric oxide. Further, as proof of principle, we have identified one target by lowering the $pO_2$. In this exemplary case, human red blood cells were exposed to anaerobiosis or room air and 50 nM NO was added. Low $pO_2$ induced an interaction of a specialized hemoglobin enzyme, that subserves NO processing, with an anion exchange protein that was identified by co-immunoprecipitation. At low but not high $pO_2$ the hemoglobin enzyme interacted with the exchanger protein to nitrosylate it. Thus $pO_2$ can regulate protein-protein interactions. Furthermore, inasmuch as we have established that nitrosylation can promote protein-protein interactions, low $O_2$/NO would operate in concerted fashion to promote multiple protein-protein interactions.

The presence of hydrogen peroxide in the determinations did not produce or modify the majority of determined interactions indicating use of body oxygen concentration instead of room air would not have made a significant difference in those cases and shows specificity for different redox modifiers.

To assess the possibility of NO-dependent regulation of protein-protein interactions in a cellular context, a modified yeast two-hybrid screening methodology was developed. The first step was to delete the yeast flavohemoglobin gene (Liu et al., 2000), which consumes NO very efficiently and thus obfuscates NO signaling. The second step was to establish three complimentary methods to identify NO-dependent protein-protein interactions, in which NO is delivered from a long-lived donor, diethyltriamine-nitric oxide (DETA-NO) (half-life ~18 hours in our assay) dispersed in solid agar (Method 1), soft agar (Method 2) or liquid medium (Method 3), thus covering a range of nitrosylating conditions (NO flux, gradient and concentration, as well as medium). It was also necessary to establish a concentration range of DETA-NO over which physiological amounts of NO could be generated in these assays without impairing yeast growth (FIG. 1A) (100 µM DETA-NO produces steady state concentrations of ~300 nM NO in yeast culture medium, as determined using an NO electrode)

One of the best examples of functional regulation by S-nitrosylation is the control of caspase-3-dependent death receptor signaling. In particular, S-nitrosylation inhibits and denitrosylation facilitates the sequential activation of caspases within macromolecular complexes (Mannick et al., 1999; Dimmeler et al., 1997; Kim et al., 1997). However, the molecular mechanism(s) of action, which enable S-nitrosylation to regulate signal transduction through these complexes, remain poorly understood. Therefore an NO-based two-hybrid screen of a CDNA library derived from cytokine-activated murine macrophages (which are widely used to study the involvement of NO in apoptosis) (Eu et al., 2000) was conducted, using procaspase-3 as bait. PCR analysis with specific primers verified that the library contained apoptosis-related cDNAs including caspase-3, 8, 9, Apaf-1, Bcl-2 and apoptosis inducing factor (AIF). Initially ~4 million transformants were screened for NO-dependent growth on medium lacking tryptophan, leucine and histidine (9). Thirty-five clones were isolated, which grew in the presence but not absence of NO, and from which prey plasmids retransfected into the bait strain (clean clones) showed at least 3-fold increases in growth in the presence of NO, whereas no growth was seen in yeast transformed with bait or prey vector alone. Of the 17 clones showing NO-dependent growth a second time, two clones also showed at least 3-fold activation of lac-Z transcription in the presence vs. absence of NO (p<0.05). Thus, these clones both activated lac-Z transcription and conferred histidine prototrophy in an NO-dependent manner. One of these clones contained a partial sequence (amino acids: 158–927) of the apoptosis-related enzyme, acid sphingomyelinase (ASM) (FIG. 1B). Thus these data establish the principle of NO-inducible protein-protein interactions and also emphasize the importance of varying nitrosylating conditions in any systematic analysis of NO-dependent protein-protein interactions.

In order to score the relative dependence on NO of the interactions with caspase-3, a set of clean clones was generated and assessed for NO-dependent growth (FIG. 1C) and β-gal activity (FIG. 1D). A more robust overall effect of NO on growth vs. β-gal activity was attributed to the low expression of lac Z in the CG-1945 strain, although it should be noted that the NO-dependent increases in both measures of protein-protein interaction were highly reproducible and significant (p<0.001). Growth was particularly robust in the iNOS transformant (~9-fold), which suggests that the NO-dependent protein-protein interactions of NOS are of comparatively high-affinity, consistent with an important and previously unsuspected autoregulatory role for NO production. Such a role would be analogous to the case of protein kinases, which have a critical self-regulatory function expressed through phosphorylation (Hunter, 2000), and implies that interactions regulated by NOS in signaling modules may be similarly regulated.

Example 2

Large Scale Yeast Two Hybrid Screening

To enable rapid large-scale screening, an alternative method of genomic two-hybrid analysis in which E. coli were transformed with plasmids pooled from yeast transformants that were previously grown for several days in histidine (HIS)-deficient medium, supplemented continuously with NO (Method 3) was developed. The prey plasmids were isolated and retransfected into caspase-3 bait strains, whose NO-dependent growth was then assessed individually. Approximately 1800 E. coli colonies were derived from a screen of ~4 million transformants; 499 of these contained prey plasmids, of which 50 appeared at least twice (as determined by HaeIII digestion). Of these, 41 showed NO-dependent growth upon retransformation, and 25 also demonstrated NO-activation of β-gal activity (>3 fold). These clones coded for the immune response gene (IRG), phosphoglycerate mutase (PGM-1), and notably, the inducible nitric oxide synthase (iNOS); the remaining inserts encoded a number of unknown amino acid sequences that typically terminated with a stop codon.

As a further means to verify the specificity of the dependence of the interactions on NO (viz. other redox-related molecules), the same 4 clones were examined for the possibility of an interaction dependent on hydrogen peroxide, which was either added repeatedly or generated continuously with glucose oxidase; however, none was found.

Thus, NO is both necessary and sufficient for inducing the interactions between caspase-3 and ASM, IRG, PGM, and iNOS.

Example 3

NO-Dependent Protein Interactions

Methods:

Immunoprecipitation:

Thirty million cells were lysed by gentle homogenization in 1 ml IP buffer (10 mM NaPi, 100 mM NaCl, 1 mM EDTA, pH 7.9, with protease inhibitor cocktail). The supernatant obtained by centrifugation at 20,000 g for 10 min was used for immunoprecipitation. Caspase-3 immunoprecipitates (2.5 µg anti-caspase-3 monoclonal antibody, Transduction Laboratories) were washed, separated on 10% SDS-PAGE, and blotted with ASM antisera (Santa Cruz Biotechnology); 5% of the sample was blotted for caspase-3.

ASM activity was measured essentially as described (E. Romiti et al., 2000), using BODIPY FL $C_5$-sphingomyelin substrate (1.5 nmol) in assay buffer: 250 mM sodium acetate, pH 5.0, 10 mM EDTA. To assay Zn-stimulated ASM activity, 0.1 mM ZnCl was used instead of 10 mM EDTA. 30 µl sample was incubated with 70 µl assay buffer at 37° C. for 1–3 hours. Reactions were terminated by adding 1.0 ml heptane and 0.29 ml isopropyl alcohol. Phases were separated by adding 0.23 ml $H_2O$. The heptane phase was washed with 0.23 ml $H_2O$. The fluorescence of the organic phase (containing BODIPY FL-ceramide) was assayed at 505/514 nm excitation/emission wavelengths (slit width=2.5).

DETA-NO pretreatment at neutral pH was followed by brief acidification (pH 5.0) to decompose the NO donor. ASM/caspase-3 co-incubations were then performed at pH 7.2.

ASM Activity is Independent of NO

Purified ASM protein (3.4 µg) was treated with DETA-NO (50 µM–200 µM for 30 or 60 min) and ASM activity was measured at pH 5.0 (n=3).

Exposure of caspase-3 to NO induces binding of ASM (n=8, single asterisk, P<0.002 vs. caspase-3/ASM without NO) (FIG. 2A). Purified caspase-3 was incubated in the presence or absence 20 µM DETA-NO for 60 min (30 nM steady state NO), followed by incubation with ASM at 37° C. for 2 hrs, and IP with caspase-3 antibody. Under the same conditions, preincubation of ASM with NO did not induce an interaction with caspase-3, and the results of incubation of both ASM and caspase-3 with NO were indistinguishable from pre-incubation of caspase-3 alone with NO (not shown). S-nitrosylation of caspase-3 by NO was separately verified by photolysis-chemiluminesence (Mannick et al., 1999). The interaction of caspase-3 with ASM was measured as ASM activity in caspase-3 IP's (pH 5.0). Little or no ASM activity was present in IP's with caspase-3 antibody of either caspase-3 or ASM in isolation.

Figure 2:
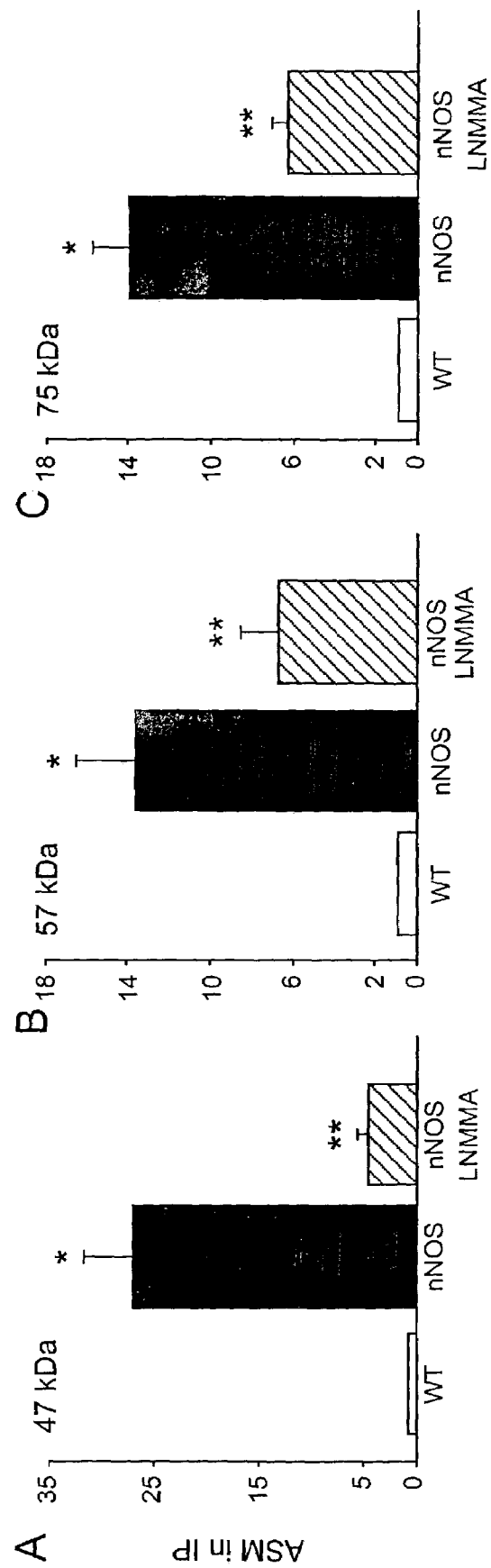
FIG. 2 illustrates that endogenous NO mediates reversible interactions between acid sphingomyelinase (ASM) and caspase-3 in mammalian cells.

Amounts of ASM isoforms (47, 57, 75 kDa) in caspase-3 immunoprecipitates (IP) from wild type (WT) vs. nNOS-expressing HEK cells were normalized with respect to the amounts of caspase-3 in the IPs (FIG. 2, bar graphs); IPs were performed in the presence and absence of the NOS inhibitor, LNMMA (3 mM). nNOS vs. WT (single asterisk, P<0.01) and nNOS vs. nNOS+LNMMA (double asterisk, p<0.05). A and B, n=7–14; C, n=3–5.

If NO-dependent protein interactions are physiologically relevant, then they should be demonstrable in mammalian cells at physiologically relevant NO concentrations. Therefore, the interaction between ASM and iNOS was focused on because of their known functional interrelatedness with caspase-3 and their role in apoptosis (Mannick et al., 1999; Kim et al., 1997; Eu et al., 2000; Mannick et al., 1994; Bulotta et al., 2001; De Nadal et al., 2000). Human embryonic kidney (HEK-293) cells were exposed to 200 µM DETA-NO, a concentration that optimally induced in yeast the interactions of caspase-3 with ASM (FIG. 1E) and with iNOS (FIG. 1F). Under these conditions, immunoprecipitation of caspase-3 brought down the 57 kD active form of ASM, whereas little or no co-precipitating ASM was seen in the absence of NO (n=4; p<0.03, data not shown). To define further the NO requirement for this interaction, caspase-3 was immunoprecipitated from wild-type HEK cells and from HEK cells stably transfected with nNOS (Bredt et al., 1992), in the presence and absence of the NOS inhibitor L-NMMA. Little or no ASM was pulled down in precipitates from wild-type HEK cells, whereas ASM was readily detected in the precipitates from nNOS-expressing cells (FIG. 2). Moreover, ASM/caspase-3 interactions were observed not only between the 57 kD mature form of ASM, but also with the ASM proform (75 kD) and a smaller processed form (47 kD), which may be alternatively regulated (Ferlinz et al., 1994; Hurwitz et al., 1994). Finally, exposure to L-NMMA significantly reduced the interaction between all isoforms of acid sphingomyelinase and caspase-3 (p<0.05) (FIG. 2).

Thus, these results demonstrate that the interaction between caspase-3 and several differentially processed isoforms of ASM is regulated in mammalian cells by endogenously produced NO. These results further indicate that this NO-regulated interaction is reversible.

Covalent modification of proteins by NO may unmask (or alter) protein interaction domains, and thus alter the affinity of interaction, and consensus sequences for S-nitrosylation (Stamler et al., 1997) in both procaspase-3 and ASM that could underlie the NO-dependence of their interaction were identified. The sequences include XCY in primary sequence (but also revealed in tertiary and quatenary structures), where X or Y are acidic and/or basic amino acids (e.g. KRHDE). An aromatic residue is frequently found in close proximity (in primary or tertiary structure e.g. HCY, in which case an additional acid or base will typically be present in 3D structure. In addition, cysteines residing within hydrophobic pockets of proteins operationally define a motif for S-nitrosylation.

Figure 3:
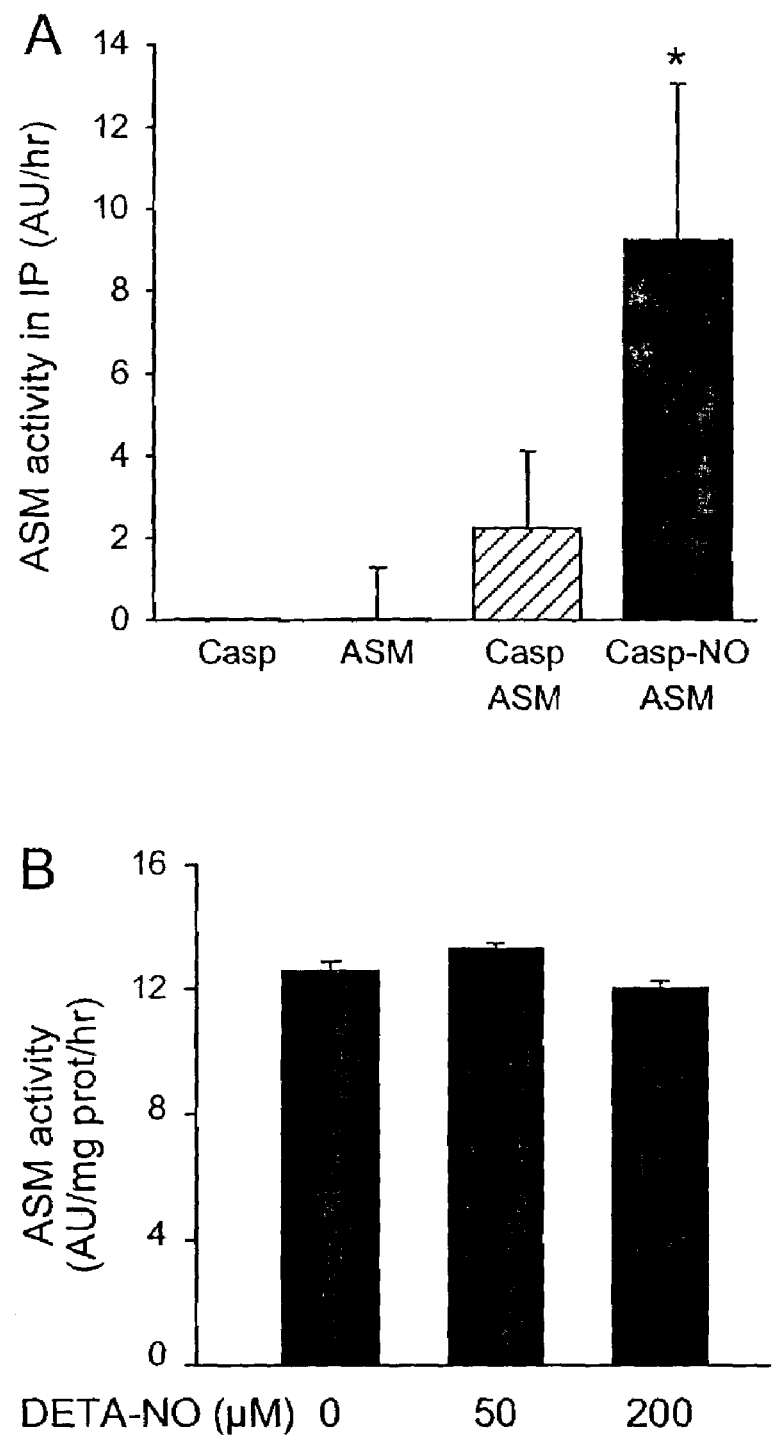
FIG. 3 illustrates an in vitro assay for determining NO-induced protein-protein interactions.

To determine the relevant target(s) of NO, ASM/caspase-3 co-precipitations were carried out following NO treatment of each partner alone. Using an ASM activity assay, the amounts of ASM that could be precipitated with a pro-caspase-3 antibody was assessed from co-incubates (2 hours at 37° C.) of ASM (20 pmol) and caspase-3 in limiting amounts (2.5 pmol). NO pretreatment was for one hour at 25° C. with 20 µM DETA-NO, generating a maximum NO concentration of 30 nM, and was followed by removal of the NO donor. As shown in FIG. 3A, procaspase-3 that had been pretreated with NO brought down significantly more ASM than did native procaspase-3 ($p<0.002$). In contrast, ASM that had been pretreated with NO did not co-precipitate caspase in increased amounts (not shown). Control studies showed that NO had no direct effect on ASM activity at these or higher concentrations (FIG. 3B), and that ASM could not be precipitated directly by caspase-3 antibody (FIG. 3A). Thus, it can be concluded that caspase-3 is the relevant target of NO and that modification by NO regulates its interaction with ASM.

Example 4

S-Nitrosylation of Caspase-3

Methods:

Immunoprecipitation:

HEK cell lysates from wild type (WT), nNOS- and eNOS-expressing cells were immunoprecipitated with caspase-3 monoclonal antibodies and blotted (IB) for nNOS, eNOS, and caspase-3, respectively. eNOS, nNOS and caspase-3 in whole cell lysates (Lysate) and in IPs from those lysates (7–20% SDS-PAGE) are shown. Data are representative of 5 similar experiments. eNOS and nNOS were not detectable in control IPs (not shown).

Amounts of eNOS in Caspase-3 IPs are Dependent on eNOS Activity eNOS-expressing HEK cells were treated with L-arginine (1 mM)/$Ca^{2+}$ (200 µM) (to activate NOS) in the presence or absence of L-NMMA (3 mM) (to inhibit NOS activation). Amounts of eNOS were quantified from scanned Western blots (7–20% SDS-PAGE) and normalized with respect to amounts of caspase in the IP (bar graph), (n=3).

It has been shown previously that procaspases in vivo are S-nitrosylated on their catalytic cysteine and thereby maintained in an inactive state (Mannick et al., 1999; Dimmeler et al., 1997; Kim et al., 1997), but from analysis of the crystal structure of caspase-3 (PDB:1PAU), this active-site modification would not be anticipated to affect protein-protein interactions. It is known, however, that caspase-3 can be S-nitrosylated on more than one cysteine residue (Zech et al., 1999), and in previous experiments, it was observed that a procaspase-3 active site mutant (C→A) was still S-nitrosylated by NO, and that clean immunoprecipitates of this catalytic site mutant from stably transfected MCF-7 cells showed that it was also nitrosylated in vivo (Mannick et al., 1999). Furthermore, wild-type caspase-3 precipitated from various human cell lines cells may be constitutively nitrosylated at more than one site. Thus S-nitrosylation of procaspase-3 at an allosteric site occurs both in vitro and in vivo.

Taken together with these findings, these results indicate that: 1) procaspase-3 and ASM exhibit a weak binding interaction, and the affinity of this protein-protein interaction is increased significantly by low nanomolar amounts of NO both in vitro and in heterologous cell systems (e.g. yeast); 2) the interaction is regulated reversibly by NOS activity in mammalian cells; and 3) the mechanism is likely to involve S-nitrosylation of an allosteric site on procaspase-3. This data is the first indication that S-nitrosylation of different sites on a protein may differentially regulate its function (e.g., allosteric or active site-thiol modification influences respectively protein-protein interactions and enzymatic activity).

Figure 4:
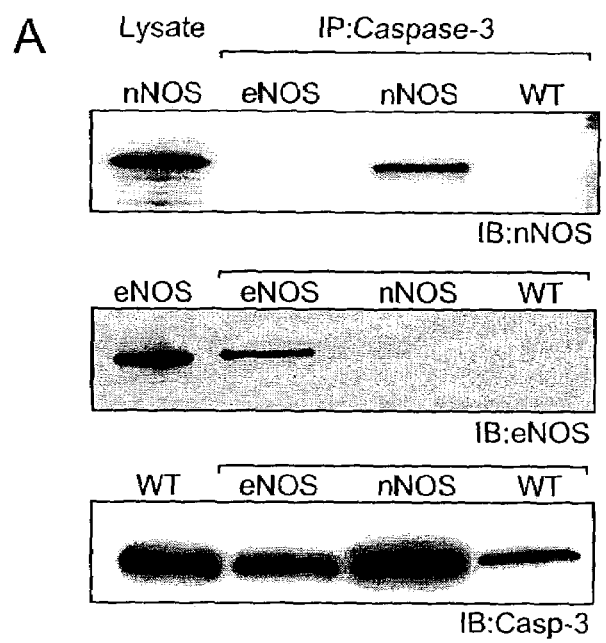
FIG. 4 illustrates dynamic NO-regulated interactions between NO synthases and caspase-3 in vivo.
Figure 4:
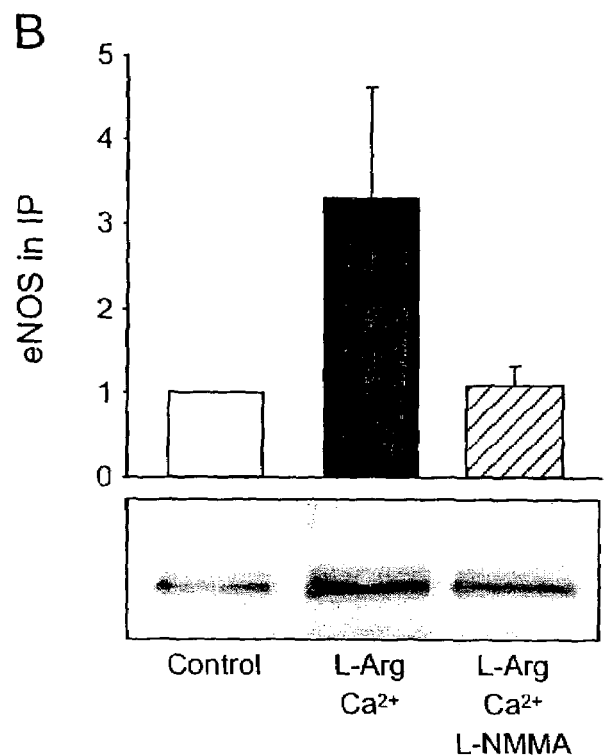

Inhibition of caspase-3 by S-nitrosylation in multiple cell types and by all three major isoforms of NOS (Mannick et al., 1999; Dimmeler et al., 1997; Kim et al., 1997) suggests that NOSs may share a common motif for recognition by caspase-3. Notably, the two iNOS clones showing an interaction with caspase-3 encode a region overlapping the oxygenase, FMN-binding and CaM-binding domains (amino acids 455–647), which is conserved among the three isoforms of NOS. Indeed, as shown in FIG. 4A, caspase-3 antibodies effectively co-precipitated nNOS or eNOS from HEK-293 cells expressing nNOS or eNOS (Bredt et al., 1992; Sessa et al., 1995). In contrast, isotype-matched control IgG did not precipitate detectable eNOS or nNOS (not shown). Moreover, it has recently been shown that regulation of caspase-3 by NOS occurs principally within mitochondria (Mannick et al., 2001). And in support of a mitochondrial connection, NOS is enriched in highly purified mitochondrial preparations from HEK cells and that NOS-dependent protein-protein interactions are indeed differentially regulated in the mitochondrial and cytosolic fractions.

Example 5

NO-Dependent Protein-Protein Interactions of NOS

Methods:

Yeast Two-Hybrid Assay

Yeast (Δyhb1) were transformed with Gal4 BD-AIF (Bait) and Gal4 AD-MIP-1α (Prey). (A) Robust growth of the AIF/MIP-1α clone requires NO (single asterisk, $P<0.001$ versus AIF/MIP-1α without NO) (n=6). In contrast, the clone expressing AIF alone shows little growth in either the presence or absence of NO. Cells were grown in His-Trp-Leu-deficient medium at 30° C. for 72 hrs with or without 200 µM DETA-NO. (B) β-galactosidase activities in samples shown in A (single asterisk, $P<0.001$ vs. without NO, n=4).

To probe further the physiological relevance of NO-dependent protein-protein interactions of NOS, the effects of NOS activity on binding of caspase-3 were assessed. It was found that L-arginine and calcium supplementation, which activate eNOS, increased its interaction with caspase-3, while L-NMMA, which inhibits NOS, almost completely reversed this effect (FIG. 4B). Thus, NOS reversibly regulates its own binding to capase-3 through NO production. Although the ramifications of these data remain to be explored fully in physiological context, NO-dependent interactions between NOSs and caspase, perhaps involving a ternary complex with ASM, would be consistent with the abundant literature on the regulatory interactions between NOSs, caspases and ASM/ceramide in various subcellular compartments (Bulotta et al., 2001; De Nadai et al., 2000; Huwiler et al., 1999; Liu et al., 1995; Igarashi et al., 1999; Takeda et al., 1999; Schwandner et al., 1998).

The demonstration that multiple protein-protein interactions of caspase-3 may be determined by NO would have far reaching implications for our understanding of the proteome if extended to other classes of protein. To extend the generality of our findings, 2.5 million transformants were screened from our macrophage cDNA library for NO-dependent interactions, using apoptosis-inducing factor (AIF) as bait. AIF is implicated in cell death that is independent of caspase-3, and is not known to be regulated by NO (Lipton et al., 2002). Eighteen clones were isolated, of which two showed NO-dependent growth upon retransfection of the prey plasmid into the bait strain (e.g., in two independent screens) as well as >3-fold increases in β-gal activity in the presence of NO. One of these clones contained the entire cDNA sequence of the chemokine, macrophage inflammatory protein-1 alpha (MIP-1α). Since this clone contained a few extra amino acids derived from a linker sequence, the full length MIP-1α coding sequence was amplified by PCR and cloned into the pGAD 10 vector, whose NO-dependent interaction with AIF was verified. The new clone showed a robust (8-fold) increase in growth in the presence of NO, whereas clones containing the bait or prey alone showed virtually no growth either in the presence of absence of NO (FIG. 5). These data suggest strongly that NO will be found to regulate a broad spectrum of protein-protein interactions.

Overall, these findings help to explain a number of experimental and clinical observations: 1) a complex involving NOS/caspase-3 would explain the observation that amounts of NO required to regulate caspase-3 in vivo are in fact below detection (Mannick et al., 1994); 2) the possibility that caspase-3 might recruit NOS/ASM would rationalize the observation that NO can co-temporally affect ASM/ceramide and caspase-3 activities (De Nadai et al., 2000); 3) the novel link between AIF and NO could explain NO-mediated apoptosis that is independent of caspase-3 (Marshall et al., 2002), and the paradox of pro- and anti-apoptotic effects of AIF reported recently (Lipton et al., 2002); 4) the caspase-3/PGM interaction might provide a basis for apoptosis-regulating effects of NO that depend on glycolysis (Almeida et al., 2001); 5) the caspase-3/IRG interaction might provide a mechanism for IRG's role in neural patterning and host defense (Lee et al., 1995; Schmidt and Richter, 2000). In addition, our findings may have therapeutic implications. For example, production of MIP-1α confers protection against macrophage trophic HIV (Cocchi et al., 2000), whereas production of NO can have the opposite effect (Mannick et al., 1999; Hermann et al., 1997). One reason might be that MIP is sequestered by AIF in NO-generating cells. MIP has also been linked to deregulated apoptosis in patients with a predisposition to malignancy and progressive bone marrow aplasia (Haneline et al., 1998), and the NO-dependent interaction with AIF could provide an explanation. Thus these data might support the use of NOS inhibitors in certain patients with malignancy, bone marrow failure or infection.

Example 6

Effect of ROSs on Atherosclerosis

Bovine endothelial cells are exposed to LDL cholesterol to induce atherosclerotic changes including production of reactive oxygen species. The predominant reactive oxygen species are identified as being superoxide and hydrogen peroxide, and used in a yeast-2 hybrid determination at $pO_2$ of about 70 to identify novel interacting partners, of which one is shown to cause cell death. Inhibiting that new protein is shown to be antiatherogenic.

Example 7

Effect of D-glucose on Endothelial Cell Function

Human umbilical vein endothelial cells are exposed to 30 millimolar D-glucose which impairs endothelial cell function as measured by loss of nitric oxide bioactivity. Increased oxidative stress is localized to the mitochondria using a fluorescent dye and superoxide is shown to be the oxidant (causing the oxidative stress). A yeast two-hybrid determination using multiple mitochondrial proteins identifies novel interactions in the presence of superoxide generated by depleting cells of arginine and/or adding paraquat as compared to determination without superoxide being present. In addition, new surface epitopes are found to be present in cells as identified by antibodies and as described in methods described above.

Example 8

Effect of Tumor Necrosis Factor (TNF) and Interferon Gamma (IFN-γ) on Protein Expression in Macrophages Macrophages exposed to TNF and interferon gamma were kept at $pO_2$ of 5 mm Hg. Protein expression was compared in 2D-gels (by differential profiling) to $pO_2$ of 100 mm Hg. A yeast 2 hybrid was then established for the proteins only expressed at low $pO_2$, showing previously unappreciated interactions.

Example 9

Redox Reactions in Pulmonary Fibrosis

The following description is an application of the methods of the invention for determining protein-protein interactions for a pathophysiological process. The pathophysiological process chosen for illustration is interstitial pulmonary fibrosis. Putative RSMMs are identified based on redox-related enzymes responsible for the generation of reactive oxygen and/or reactive nitrogen species in pulmonary fibroblast cells, e.g., in response to platelet derived growth factor causing fibrosis. From these enzymes, the redox-state modifier molecules that cause injury and/or the type of protein modification that is most prevalent are determined. Any protein known to be involved in fibroproliferative disorders in the lung is used as bait. All proteins or genes expressed in pulmonary fibroblast cells (cDNA library) are used as prey. As a further measure of specificity, only those genes or proteins that are highly expressed in fibroproliferative disorders, as identified by differential profiling, are utilized. A yeast two-hybrid system determination is carried out at a body oxygen concentration as determined in pulmonary fibrosis tissue with exposing of the system to the RSMMs identified above as causing injury and/or the type of protein modification that is most prevalent, to identify new binding partners, and/or inhibition of other binding, and thus new drug targets. Alternatively, antibodies are generated to cell epitopes before and after production of reactive oxygen species and new epitopes are thereby discovered.

Those skilled in the art will recognize, or be able to ascertain using no more than routine experimentation, many equivalents to the specific embodiments of the invention specifically described herein. Such equivalents are intended to be encompassed in the scope of the following claims.

We claim:

1. A method for identifying an agent capable of inhibiting a redox state modifier molecule (RSMM) induced multi-protein complex comprising:
   (a) culturing a first cell in a media comprising an RSMM and a test agent;
   (b) culturing a second cell in a media comprising the RSMM and without the test agent;
   (c) analyzing the first cell to determine the existence of the RSMM induced multi-protein complex;
wherein the agent is identified when the RSMM induced multi-protein complex does not exist or exists to a lesser degree in the first cell than the protein complex that exists in the second cell.

2. The method of claim 1 in which the RSMM is selected from the group consisting of nitric oxide, nitric dioxide, dinitrogen trixide, dinitrogen tetraoxide, S-nitrosothiol, nitroxyl anion, HNO, nitrite, nitrate, C—, N, O, S or metal-nitroso or nitro compounds, hydrogen peroxide, peroxynitrite, other peroxides, alkoxides, superoxide, hypochlorite ion, hydroxyl radical and physiological $pO_2$.

3. The method as in claim 2 wherein the pO2 is in a range from about 5 to about 100 mm Hg.

4. The method of claim 3 wherein the range is from about 10 to about 50 mm Hg.

5. The method of claim 4 wherein the range is from about 10 to about 30 mm Hg.

6. The method as in claim 1 in which the RSMM is an NO adduct.

7. The method of claim 6 wherein the NO adduct is selected from the group consisting of DETA-NO, S-nitrosothiol, SIN-1, angeli's salt, S-nitroso amino acids, S-nitroso-polypeptides, and nitrosoamines.

8. A method for identifying a compound capable of modulating a protein-protein interaction comprising:
   (a) providing a cell culture media containing at least one RSMM;
   (b) culturing a cell that expresses a first protein and a second protein in the cell culture media containing at least one RSMM, wherein an interaction between the first protein and second protein produces a first detectable signal, and wherein the interaction is induced by the presence of the RSMM;
   (c) contacting the cell with the compound wherein an interaction between the first protein and the second protein produces a second detectable signal, wherein the second detectable signal being lower than the first detectable signal is an indication that the compound is capable of modulating the interaction between the first and second protein.

9. The method of claim 8 wherein the RSMM is selected from the group consisting of nitric oxide, nitric dioxide, hydrogen peroxide, superoxide, hypochlorite ion, hydroxyl radical and physiological $pO_2$.

10. The method of claim 9 wherein the pO2 is in a range from about 5 to about 100 mm Hg.

11. The method of claim 10 wherein the range is from about 10 to about 50 mm Hg.

12. The method of claim 10 wherein the range is from about 10 to about 30 mm Hg.

13. The method of claim 8 wherein the RSMM is an NO adduct.

14. The method of claim 13 wherein the NO adduct is DETA-NO, S-nitrosothiol, S-nitroso amino acids, S-nitroso-polypeptides, and nitrosoamines.

15. The method of claim 8 further comprising performing a growth assay on the cell in the presence and absence of the RSMM.

16. The method of claim 8 wherein the cell culture media comprises an RSMM concentration of 1 nM to 1000 μM.

17. The method of claim 8 further comprising the step of altering the concentration of the RSMM during culturing.

18. The method of claim 17 wherein the alteration is an increase in the concentration of the RSMM.

19. The method of claim 17 wherein the alteration is a decrease in the concentration of the RSMM.

20. The method of claim 8 wherein there is more than one RSMM provided to the cell.

21. The method of claim 8 wherein at least one RSMM is nitric oxide.

22. The method of claim 8 wherein the cell is a yeast cell.

23. The method of claim 22 wherein the yeast cell is *S. cerevisiae*.

24. The method of claim 22 wherein the yeast cell does not express a functional flavohemoglobin gene.

25. The method of claim 8 wherein the first protein and the second protein are recombinantly expressed.

26. The method of claim 8 wherein the first protein or the second protein is a prey protein.

27. The method of claim 8 wherein the first protein or the second protein is a bait protein.

28. The method of claim 8 wherein the first detectable signal or second detectable signal is detected by a colorimetric assay.

29. The method of claim 8 wherein the interaction of the first protein and the second protein is determined by a yeast two hybrid assay detection.

30. The method of claim 8 wherein the first protein and the second protein are involved in cell death or cell growth.

31. The method of claim 8 where the first protein and the second protein are cell division cycle proteins.

32. A method for identifying a compound capable of modulating a protein-protein interaction comprising:
(a) providing a cell culture media containing at least one RSMM;
(b) culturing a cell that expresses a first protein and a second protein in the cell culture media containing at least one RSMM, wherein an interaction between the first protein and second protein produces a first detectable signal;
(c) contacting the cell with the compound wherein an interaction between the first protein and the second protein produces a second detectable signal, wherein the second detectable signal being lower than the first detectable signal is an indication that the compound is capable of modulating the interaction between the first and second protein; and
wherein the pO2 is in a range from about 5 to about 100 mm Hg.

33. The method of claim 32 wherein the RSMM is selected from the group consisting of nitric oxide, nitric dioxide, hydrogen peroxide, superoxide, hypochlorite ion, hydroxyl radical and physiological $pO_2$.

34. The method of claim 32 wherein the RSMM is an NO adduct.

35. The method of claim 34 wherein the NO adduct is DETA-NO, S-nitrosothiol, S-nitroso amino acids, S-nitrosopolypeptides, and nitrosoamines.

36. The method of claim 32 wherein the range is from about 10 to about 30 mm Hg.

37. The method of claim 32 further comprising performing a growth assay on the cell in the presence and absence of the RSMM.

38. The method of claim 32 wherein the cell culture media comprises an RSMM concentration of 1 nM to 1000 μM.

39. The method of claim 32 further comprising the step of altering the concentration of the RSMM during culturing.

40. The method of claim 39 wherein the alteration is an increase in the concentration of the RSMM.

41. The method of claim 39 wherein the alteration is a decrease in the concentration of the RSMM.

42. The method of claim 32 wherein there is more than one RSMM provided to the cell.

43. The method of claim 32 wherein at least one RSMM is nitric oxide.

44. The method of claim 32 wherein the cell is a yeast cell.

45. The method of claim 44 wherein the yeast cell is *S. cerevisiae*.

46. The method of claim 44 wherein the yeast cell does not express a functional flavohemoglobin gene.

47. The method of claim 32 wherein the first protein and the second protein are recombinantly expressed.

48. The method of claim 32 wherein the first protein or the second protein is a prey protein.

49. The method of claim 32 wherein the first protein or the second protein is a bait protein.

50. The method of claim 32 wherein the first detectable signal or second detectable signal is detected by a colorimetric assay.

51. The method of claim 32 wherein the interaction of the first protein and the second protein is determined by a yeast two hybrid assay detection.

52. The method of claim 32 wherein the first protein and the second protein are involved in cell death or cell growth.

53. The method of claim 32 where the first protein and the second protein are cell division cycle proteins.

* * * * *